US011446407B2

(12) United States Patent
Jonn et al.

(10) Patent No.: US 11,446,407 B2
(45) Date of Patent: *Sep. 20, 2022

(54) ADHESIVE-CONTAINING WOUND CLOSURE DEVICE AND METHOD

(71) Applicant: Ethicon, Inc., Somerville, NJ (US)

(72) Inventors: Jerry Y. Jonn, Raleigh, NC (US); Julian Quintero, Flemington, NJ (US); Glenn Hoskin, Apex, NC (US)

(73) Assignee: Ethicon, Inc., Raritan, NJ (US)

( * ) Notice: Subject to any disclaimer, the term of this patent is extended or adjusted under 35 U.S.C. 154(b) by 215 days.

This patent is subject to a terminal disclaimer.

(21) Appl. No.: 16/556,471

(22) Filed: Aug. 30, 2019

(65) Prior Publication Data

US 2019/0381206 A1     Dec. 19, 2019

Related U.S. Application Data

(60) Continuation of application No. 15/452,126, filed on Mar. 7, 2017, now Pat. No. 10,398,800, which is a division of application No. 12/163,021, filed on Jun. 27, 2008, now Pat. No. 9,623,142, which is a division of application No. 10/887,884, filed on Jul. 12, 2004, now abandoned.

(51) Int. Cl.
| A61L 15/58 | (2006.01) |
| A61L 15/24 | (2006.01) |
| A61L 15/42 | (2006.01) |
| A61L 15/44 | (2006.01) |

(52) U.S. Cl.
CPC ............ *A61L 15/58* (2013.01); *A61L 15/24* (2013.01); *A61L 15/425* (2013.01); *A61L 15/44* (2013.01); *Y10T 442/10* (2015.04); *Y10T 442/172* (2015.04); *Y10T 442/183* (2015.04); *Y10T 442/20* (2015.04)

(58) Field of Classification Search
CPC .. A61B 17/085; A61F 13/0246; A61F 13/025; A61F 13/0253; A61F 13/0203; A61F 13/023; A61L 24/06; A61L 24/001; A61L 24/0036; A61L 24/0042; A61L 2400/16
See application file for complete search history.

(56) References Cited

U.S. PATENT DOCUMENTS

| 167,162 A | 8/1875 | French |
| 1,656,199 A | 1/1928 | Ensley |
| 2,399,545 A | 4/1946 | Davis |
| 2,508,855 A | 5/1950 | Brown |
| 2,721,858 A | 10/1955 | Joyner et al. |
| 2,722,220 A | 11/1955 | Mestrand |
| 2,807,262 A | 9/1957 | Lew |
| 2,905,174 A | 5/1959 | Smith |
| 3,085,572 A | 4/1963 | Blackford |
| 3,254,111 A | 5/1966 | Hawkins et al. |
| 3,330,275 A | 7/1967 | Jenard et al. |
| 3,402,716 A | 9/1968 | Baxter |
| 3,520,300 A | 7/1970 | Flower, Jr. |
| 3,731,683 A | 5/1973 | Zaffaroni |
| 3,888,247 A | 6/1975 | Stenvall |
| 3,940,362 A | 2/1976 | Overhults |
| 3,983,878 A | 10/1976 | Kawchitch |
| 3,995,641 A | 12/1976 | Kronenthal et al. |
| 4,068,664 A | 1/1978 | Sharp et al. |
| 4,080,348 A | 3/1978 | Korpman |
| 4,126,130 A | 11/1978 | Cowden et al. |
| 4,140,115 A | 2/1979 | Schonfeld |
| 4,263,906 A | 4/1981 | Finley |
| 4,313,865 A | 2/1982 | Teramoto et al. |
| 4,340,043 A | 7/1982 | Seymour |
| 4,364,876 A | 12/1982 | Kimura et al. |
| 4,390,519 A | 6/1983 | Sawyer et al. |
| 4,460,369 A | 7/1984 | Seymour |
| 4,560,723 A | 12/1985 | Millet et al. |
| 4,584,355 A | 4/1986 | Blizzard et al. |
| 4,585,836 A | 4/1986 | Homan et al. |
| 4,591,622 A | 5/1986 | Blizzard et al. |
| 4,612,230 A | 9/1986 | Liland et al. |
| 4,614,183 A | 9/1986 | McCracken et al. |
| 4,630,603 A | 12/1986 | Greenway |
| 4,655,767 A | 4/1987 | Woodard et al. |
| 4,671,266 A | 6/1987 | Legnyel et al. |
| 4,720,513 A | 1/1988 | Kameyama et al. |
| 4,728,380 A | 1/1988 | Jones |
| 4,733,659 A | 3/1988 | Edenbaum et al. |

(Continued)

FOREIGN PATENT DOCUMENTS

| AU | 2005-215776 A | 9/2005 |
| CA | 2262408 A | 8/2000 |

(Continued)

OTHER PUBLICATIONS

U.S. Appl. No. 10/779,721, filed Feb. 18, 2004, US-2005-0182443-A1, Abandoned.
U.S. Appl. No. 10/887,884, filed Jul. 12, 2004, US-2006-0009099-A1, Abandoned.
U.S. Appl. No. 12/163,021, filed Jun. 27, 2008, US-2008-0255610-A1, U.S. Pat. No. 9,623,142, Apr. 18, 2017, Grant.
U.S. Appl. No. 12/207,984, filed Sep. 10, 2008, US-2009-0076542-A1, U.S. Pat. No. 9,655,622, May 23, 2017, Grant.
U.S. Appl. No. 14/864,033, filed Sep. 24, 2015, US2016-0089145, Abandoned.
U.S. Appl. No. 15/280,303, filed Sep. 29, 2016, US-2018-0085259, U.S. Pat. No. 10,470,934, Nov. 12, 2019, Grant.

(Continued)

*Primary Examiner* — Alexander J Orkin

(57) ABSTRACT

An article, such as a tissue bonding article, includes a flexible material, a polymerization initiator or rate modifier disposed in or on the flexible material, and a polymerizable adhesive composition permeated throughout at least a portion of the flexible material, where the polymerization initiator or rate modifier is a polymerization initiator or rate modifier for the polymerizable adhesive composition.

10 Claims, No Drawings

(56) References Cited

U.S. PATENT DOCUMENTS

| | | |
|---|---|---|
| 4,767,401 A | 8/1988 | Seiderman |
| 4,793,887 A | 12/1988 | Card et al. |
| 4,793,888 A | 12/1988 | Card et al. |
| 4,795,435 A | 1/1989 | Steer et al. |
| 4,852,571 A | 8/1989 | Gadsby et al. |
| 4,867,747 A | 9/1989 | Yarger |
| 4,872,450 A | 10/1989 | Austad |
| 4,950,282 A | 8/1990 | Beisang et al. |
| 4,966,605 A | 10/1990 | Thieler |
| 4,999,235 A | 3/1991 | Lunn et al. |
| 5,035,687 A | 7/1991 | Sandbank |
| 5,059,424 A | 10/1991 | Cartmell et al. |
| 5,086,763 A | 2/1992 | Hathman |
| 5,088,483 A | 2/1992 | Heinecke |
| 5,106,362 A | 4/1992 | Gilman |
| 5,125,907 A | 6/1992 | Philpott |
| 5,164,444 A | 11/1992 | Bernard |
| 5,173,302 A | 12/1992 | Holmblad et al. |
| 5,232,958 A | 8/1993 | Mallya et al. |
| 5,254,132 A | 10/1993 | Barley et al. |
| 5,259,835 A * | 11/1993 | Clark .................. A61F 13/0246 602/48 |
| 5,266,371 A | 11/1993 | Sugii et al. |
| D347,059 S | 5/1994 | Mota |
| 5,308,313 A | 5/1994 | Karami et al. |
| 5,328,687 A | 7/1994 | Leung et al. |
| 5,336,209 A | 8/1994 | Porzilli |
| 5,415,626 A | 5/1995 | Goodman et al. |
| 5,429,592 A | 7/1995 | Jensen |
| 5,445,597 A | 8/1995 | Clark et al. |
| 5,449,340 A | 9/1995 | Tollini |
| D363,126 S | 10/1995 | Dusek |
| 5,456,660 A | 10/1995 | Reich et al. |
| 5,476,440 A | 12/1995 | Edenbaum |
| 5,486,547 A | 1/1996 | Matsuda et al. |
| D370,258 S | 5/1996 | Newman |
| D373,750 S | 9/1996 | Gunderson |
| 5,571,079 A | 11/1996 | Bello et al. |
| 5,575,997 A | 11/1996 | Leung et al. |
| 5,582,834 A | 12/1996 | Leung et al. |
| 5,599,858 A | 2/1997 | Buchanan et al. |
| 5,620,702 A | 4/1997 | Podell et al. |
| 5,623,011 A | 4/1997 | Bernard |
| 5,624,669 A | 4/1997 | Leung et al. |
| D382,343 S | 8/1997 | Wandell et al. |
| 5,653,769 A | 8/1997 | Barley, Jr. et al. |
| D383,211 S | 9/1997 | Dunshee et al. |
| 5,662,599 A | 9/1997 | Reich et al. |
| D387,169 S | 12/1997 | Dunshee et al. |
| D389,244 S | 1/1998 | Dunshee et al. |
| 5,705,551 A | 1/1998 | Sasaki et al. |
| D391,639 S | 3/1998 | Dunshee et al. |
| 5,749,895 A | 5/1998 | Sawyer et al. |
| 5,762,955 A | 6/1998 | Smith |
| 5,780,048 A | 7/1998 | Lee |
| 5,782,788 A | 7/1998 | Widemire |
| 5,823,983 A | 10/1998 | Rosofsky |
| 5,823,986 A | 10/1998 | Peterson |
| D402,371 S | 12/1998 | Haynes et al. |
| D403,425 S | 12/1998 | Hinds |
| D404,139 S | 1/1999 | Young |
| 5,861,348 A | 1/1999 | Kase |
| 5,876,745 A | 3/1999 | Muraoka et al. |
| 5,902,443 A | 5/1999 | Kanakubo et al. |
| 5,928,611 A | 7/1999 | Leung |
| 5,931,800 A | 8/1999 | Rasmussen et al. |
| 5,947,917 A | 9/1999 | Carté et al. |
| 5,947,998 A | 9/1999 | Cartmell et al. |
| 5,951,505 A | 9/1999 | Gilman et al. |
| 5,998,694 A | 12/1999 | Jensen et al. |
| D424,699 S | 5/2000 | Allen |
| 6,093,465 A | 7/2000 | Gilchrist et al. |
| 6,125,265 A | 9/2000 | Yamamoto et al. |
| 6,140,548 A | 10/2000 | Hansen et al. |
| 6,143,352 A | 11/2000 | Clark et al. |
| 6,155,265 A | 12/2000 | Hammerslag |
| 6,183,593 B1 | 2/2001 | Narang et al. |
| D439,973 S | 4/2001 | Choksi |
| 6,217,603 B1 | 4/2001 | Clark et al. |
| 6,238,692 B1 | 5/2001 | Smith |
| 6,245,960 B1 | 6/2001 | Eaton |
| 6,284,941 B1 | 9/2001 | Cox et al. |
| 6,310,166 B1 | 10/2001 | Hickey et al. |
| 6,329,564 B1 | 12/2001 | Lebner |
| 6,352,704 B1 | 3/2002 | Nicholson et al. |
| D458,687 S | 6/2002 | Dale |
| 6,410,818 B1 | 6/2002 | Oyaski |
| 6,439,789 B1 | 8/2002 | Balance et al. |
| D463,564 S | 9/2002 | Siegwart et al. |
| 6,455,064 B1 * | 9/2002 | Narang ................ A61K 9/0014 424/443 |
| 6,479,725 B1 | 11/2002 | Brothers |
| 6,482,431 B2 | 11/2002 | Smith |
| 6,512,023 B1 | 1/2003 | Malofsky |
| D471,984 S | 3/2003 | Dunshee |
| D472,319 S | 3/2003 | Oltmann |
| 6,559,350 B1 | 5/2003 | Tetreault et al. |
| 6,579,469 B1 | 6/2003 | Nicholson et al. |
| 6,582,713 B2 | 6/2003 | Newell et al. |
| D477,076 S | 7/2003 | Wall |
| 6,589,269 B2 | 7/2003 | Zhu et al. |
| 6,595,940 B1 * | 7/2003 | D'Alessio ........... A61M 35/003 604/3 |
| 6,596,917 B2 | 7/2003 | Oyaski |
| 6,599,318 B1 | 7/2003 | Gabbay |
| 6,620,846 B1 | 9/2003 | Jonn et al. |
| D480,879 S | 10/2003 | Boehm |
| 6,632,450 B1 | 10/2003 | Gregory |
| 6,635,272 B2 | 10/2003 | Leaderman |
| 6,652,559 B1 | 11/2003 | Tetreault et al. |
| 6,667,051 B1 | 12/2003 | Gregory |
| 6,712,839 B1 | 3/2004 | Lönne |
| 6,787,682 B2 | 9/2004 | Gilman |
| 6,837,027 B2 | 1/2005 | Hickey |
| 6,841,716 B1 | 1/2005 | Tsutsumi |
| 6,942,683 B2 | 9/2005 | Dunshee |
| D515,701 S | 2/2006 | Horhota |
| D516,728 S | 3/2006 | Wall |
| D520,639 S | 5/2006 | Dodd et al. |
| 7,041,124 B2 | 5/2006 | Purcell |
| 7,044,982 B2 | 5/2006 | Milbocker |
| 7,066,934 B2 | 6/2006 | Kirsch |
| 7,122,712 B2 | 10/2006 | Lutri et al. |
| 7,144,390 B1 | 12/2006 | Hannigan et al. |
| 7,164,054 B2 | 1/2007 | Mori et al. |
| D548,348 S | 8/2007 | Nash |
| 7,252,837 B2 | 8/2007 | Guo et al. |
| D562,461 S | 2/2008 | Nash et al. |
| 7,371,400 B2 | 5/2008 | Borenstein et al. |
| D574,962 S | 8/2008 | Atkins et al. |
| D580,553 S | 11/2008 | Nash |
| D581,467 S | 11/2008 | Winningham |
| 7,457,667 B2 | 11/2008 | Skiba |
| D582,561 S | 12/2008 | Sachi |
| D584,415 S | 1/2009 | Sachi |
| 7,576,257 B2 | 8/2009 | LaGreca, Sr. |
| D611,156 S | 3/2010 | Dunshee |
| 7,713,463 B1 | 5/2010 | Reah et al. |
| D618,810 S | 6/2010 | Tanigawa et al. |
| D621,052 S | 8/2010 | Kase |
| D621,053 S | 8/2010 | Kase |
| D624,190 S | 9/2010 | Neri |
| D632,398 S | 2/2011 | Bray |
| D636,881 S | 4/2011 | Clemens |
| 7,943,811 B2 | 5/2011 | Da Silva Macedo, Jr. |
| 7,981,136 B2 | 7/2011 | Weiser |
| 7,982,087 B2 | 7/2011 | Greener et al. |
| D646,789 S | 10/2011 | Barth |
| 8,343,606 B2 | 1/2013 | Marchitto et al. |
| 8,353,966 B2 | 1/2013 | Day et al. |
| D676,490 S | 2/2013 | Bratter |
| 8,372,051 B2 | 2/2013 | Scholz |
| D679,098 S | 4/2013 | Ogawa |
| D679,402 S | 4/2013 | Conrad-Vlasak et al. |

(56) References Cited

U.S. PATENT DOCUMENTS

| | | |
|---|---|---|
| D679,403 S | 4/2013 | Heinecke et al. |
| D679,405 S | 4/2013 | Arbesman |
| D679,819 S | 4/2013 | Peron |
| D679,820 S | 4/2013 | Peron |
| D685,484 S | 7/2013 | Brambilla |
| 8,528,730 B2 | 9/2013 | Grossman |
| D691,730 S | 10/2013 | Smith et al. |
| D692,566 S | 10/2013 | Adoni |
| D693,010 S | 11/2013 | Mosa et al. |
| D694,892 S | 12/2013 | Chan et al. |
| 8,603,053 B2 | 12/2013 | Riesinger |
| D697,216 S | 1/2014 | Chan et al. |
| 8,642,831 B2 | 2/2014 | Larsen et al. |
| 8,663,171 B2 | 3/2014 | Tambourgi et al. |
| D705,429 S | 5/2014 | Cheney |
| D707,829 S | 6/2014 | Chan et al. |
| D708,751 S | 7/2014 | Chan et al. |
| 8,777,986 B2 | 7/2014 | Straehnz et al. |
| D712,045 S | 8/2014 | Thornton |
| D713,967 S | 9/2014 | Adoni |
| D715,534 S | 9/2014 | Manley |
| D714,575 S | 10/2014 | Mah |
| 8,884,094 B2 | 11/2014 | Lockwood et al. |
| D718,812 S | 12/2014 | Sukhbaatar |
| 9,000,251 B2 | 4/2015 | Murphy et al. |
| RE45,510 E | 5/2015 | Hisamitsu |
| D728,803 S | 5/2015 | Sinda et al. |
| D745,688 S | 12/2015 | Chan et al. |
| D745,689 S | 12/2015 | Chan et al. |
| D746,479 S | 12/2015 | Arefieg |
| RE45,864 E | 1/2016 | Peron |
| D746,996 S | 1/2016 | Karlsson |
| D750,789 S | 3/2016 | Mackay et al. |
| D757,950 S | 5/2016 | Karlsson et al. |
| 9,339,417 B2 | 5/2016 | Ogawa |
| 9,381,284 B2 | 7/2016 | Cornet et al. |
| 9,440,010 B2 | 9/2016 | Locke |
| 9,492,171 B2 | 11/2016 | Patenaude |
| 9,623,142 B2 * | 4/2017 | Jonn ........................ A61L 15/24 |
| D786,350 S | 5/2017 | Nakai |
| D786,351 S | 5/2017 | Nakai |
| D786,352 S | 5/2017 | Nakai |
| D786,353 S | 5/2017 | Nakai |
| D786,972 S | 5/2017 | Nakai |
| 9,655,622 B2 * | 5/2017 | Jonn ................ A61B 17/00491 |
| D790,071 S | 6/2017 | Ahsani |
| D824,525 S | 7/2018 | Lacy |
| D833,526 S | 11/2018 | Nakai |
| 10,434,211 B2 * | 10/2019 | Jonn ................ A61B 17/00491 |
| 10,470,935 B2 | 11/2019 | Quintero |
| 2001/0002432 A1 | 5/2001 | Bugge |
| 2001/0028943 A1 | 10/2001 | Mashiko et al. |
| 2001/0037077 A1 | 11/2001 | Wiemken |
| 2002/0018689 A1 | 2/2002 | Badejo et al. |
| 2002/0019652 A1 | 2/2002 | DaSilva et al. |
| 2002/0037310 A1 | 3/2002 | Jonn et al. |
| 2002/0039867 A1 | 4/2002 | Curro et al. |
| 2002/0049503 A1 | 4/2002 | Milbocker |
| 2002/0185396 A1 | 12/2002 | Mainwaring et al. |
| 2002/0192107 A1 | 12/2002 | Hickey |
| 2002/0193721 A1 | 12/2002 | VanDruff |
| 2003/0031499 A1 | 2/2003 | Heard et al. |
| 2003/0050590 A1 | 3/2003 | Kirsch |
| 2003/0093024 A1 | 5/2003 | Falleiros et al. |
| 2003/0100955 A1 | 5/2003 | Greenawalt et al. |
| 2003/0109819 A1 | 6/2003 | Tsuruda et al. |
| 2003/0125654 A1 | 7/2003 | Malik |
| 2003/0175824 A1 | 9/2003 | Pishko et al. |
| 2003/0220596 A1 | 11/2003 | Dunshee |
| 2003/0225355 A1 | 12/2003 | Butler |
| 2004/0001879 A1 | 1/2004 | Guo et al. |
| 2004/0060867 A1 | 4/2004 | Kriksunov et al. |
| 2004/0106888 A1 | 6/2004 | Lutri et al. |
| 2004/0120849 A1 | 6/2004 | Stewart et al. |
| 2004/0142041 A1 | 7/2004 | MacDonald et al. |
| 2004/0162512 A1 | 8/2004 | Liedtke et al. |
| 2004/0220505 A1 | 11/2004 | Worthley |
| 2005/0015036 A1 | 1/2005 | Lutri et al. |
| 2005/0043820 A1 | 2/2005 | Browning |
| 2005/0085757 A1 | 4/2005 | Santanello |
| 2005/0147457 A1 | 7/2005 | Badejo et al. |
| 2005/0153090 A1 | 7/2005 | Marchitto et al. |
| 2005/0154340 A1 | 7/2005 | Schlussel |
| 2005/0182443 A1 | 8/2005 | Jonn et al. |
| 2005/0208100 A1 | 9/2005 | Weber et al. |
| 2005/0288706 A1 | 12/2005 | Widomski et al. |
| 2006/0009099 A1 | 1/2006 | Jonn et al. |
| 2006/0058721 A1 | 3/2006 | Lebner et al. |
| 2006/0141012 A1 | 6/2006 | Gingras |
| 2006/0173394 A1 | 8/2006 | Stroock et al. |
| 2006/0265005 A1 | 11/2006 | Beese |
| 2007/0106195 A1 | 5/2007 | Marcoux et al. |
| 2007/0218101 A1 | 9/2007 | Johnson et al. |
| 2007/0272211 A1 | 11/2007 | Kassner |
| 2007/0282238 A1 | 12/2007 | Madsen et al. |
| 2007/0299542 A1 | 12/2007 | Mathisen et al. |
| 2008/0051687 A1 | 2/2008 | Rogers |
| 2008/0154168 A1 | 2/2008 | Lutri |
| 2008/0086113 A1 | 4/2008 | Tenney et al. |
| 2008/0109034 A1 | 5/2008 | Mather et al. |
| 2008/0110961 A1 | 5/2008 | Voegele et al. |
| 2008/0167633 A1 | 7/2008 | Vannucci |
| 2008/0228219 A1 | 9/2008 | Weiser |
| 2008/0228220 A1 | 9/2008 | Weiser |
| 2008/0280037 A1 | 11/2008 | Sheridan et al. |
| 2008/0302487 A1 | 12/2008 | Goodman et al. |
| 2009/0074842 A1 | 3/2009 | Hsu |
| 2010/0106120 A1 | 4/2010 | Holm |
| 2010/0198161 A1 | 8/2010 | Propp |
| 2010/0262091 A1 | 10/2010 | Larsson |
| 2010/0298791 A1 | 11/2010 | Jones et al. |
| 2011/0047766 A1 | 3/2011 | McAulay et al. |
| 2011/0071415 A1 | 3/2011 | Karwoski et al. |
| 2011/0092874 A1 | 4/2011 | Baschnagel |
| 2011/0130699 A1 | 6/2011 | Madsen et al. |
| 2011/0208102 A1 | 8/2011 | Chawki |
| 2011/0253303 A1 | 10/2011 | Miyachi et al. |
| 2012/0052230 A1 | 3/2012 | Olsson et al. |
| 2012/0220912 A1 | 8/2012 | Shang |
| 2012/0238933 A1 | 9/2012 | Murphy et al. |
| 2012/0277645 A1 | 11/2012 | Kikuta et al. |
| 2013/0012988 A1 | 1/2013 | Blume et al. |
| 2013/0041337 A1 | 2/2013 | Aali et al. |
| 2013/0066365 A1 | 3/2013 | Belson et al. |
| 2013/0084323 A1 | 4/2013 | Riebman et al. |
| 2013/0138068 A1 | 5/2013 | Hu et al. |
| 2013/0143326 A1 | 6/2013 | Tai et al. |
| 2013/0144399 A1 | 6/2013 | Tai et al. |
| 2013/0204077 A1 | 8/2013 | Nagale et al. |
| 2013/0218125 A1 | 8/2013 | Stopek et al. |
| 2013/0245784 A1 | 9/2013 | Tan et al. |
| 2013/0274717 A1 | 10/2013 | Dunn |
| 2013/0282049 A1 | 10/2013 | Peterson et al. |
| 2013/0317405 A1 | 11/2013 | Ha et al. |
| 2014/0024989 A1 | 1/2014 | Ueda |
| 2014/0107561 A1 | 4/2014 | Dorian et al. |
| 2014/0121649 A1 | 5/2014 | Calco |
| 2014/0155916 A1 | 6/2014 | Hodgkinson et al. |
| 2014/0171888 A1 | 6/2014 | Croizat et al. |
| 2014/0257348 A1 | 9/2014 | Priewe et al. |
| 2014/0257517 A1 | 9/2014 | Deichmann et al. |
| 2015/0057491 A1 | 2/2015 | Goddard et al. |
| 2015/0209186 A1 | 7/2015 | Abbott et al. |
| 2015/0257938 A1 | 9/2015 | Pensier |
| 2015/0297413 A1 | 10/2015 | Blanco |
| 2015/0314114 A1 | 11/2015 | La Rosa |
| 2015/0351767 A1 | 12/2015 | Zoll et al. |
| 2016/0030248 A1 | 2/2016 | Potters |
| 2016/0089145 A1 | 3/2016 | Quintero et al. |
| 2016/0296673 A1 | 10/2016 | Sambusseti |
| 2017/0035422 A1 | 2/2017 | Belson |
| 2017/0056568 A1 | 3/2017 | Shelton, IV et al. |
| 2017/0056569 A1 | 3/2017 | Vendely et al. |
| 2017/0189159 A1 | 7/2017 | Bartee et al. |

(56) References Cited

U.S. PATENT DOCUMENTS

| | | | |
|---|---|---|---|
| 2017/0273837 A1 | 9/2017 | Brueckner | |
| 2017/0367806 A1 | 12/2017 | Gingras et al. | |
| 2018/0085103 A1 | 3/2018 | Quintero et al. | |
| 2018/0085259 A1 | 3/2018 | Quintero | |
| 2018/0085260 A1 | 3/2018 | Quintero | |
| 2019/0381207 A1* | 12/2019 | Jonn | A61F 13/0203 |

FOREIGN PATENT DOCUMENTS

| | | |
|---|---|---|
| CN | 1697639 A | 11/2005 |
| CN | 201441532 U | 4/2010 |
| CN | 101965169 A | 2/2011 |
| CN | 102755216 A | 10/2012 |
| CN | 102781433 A | 11/2012 |
| CN | 203234898 A | 10/2013 |
| CN | 204766892 U | 11/2015 |
| DE | 1491205 A1 | 2/1969 |
| DE | 20122236 U1 | 11/2004 |
| EP | 0532275 A | 3/1993 |
| EP | 0730874 A | 9/1996 |
| EP | 0746293 A | 12/1996 |
| EP | 1161212 A | 8/2000 |
| EP | 2359782 A | 8/2011 |
| EP | 2377498 A | 10/2011 |
| EP | 2731563 A | 5/2014 |
| EP | 2531155 A | 10/2014 |
| EP | 2805698 A | 11/2014 |
| EP | 3574875 A1 | 12/2019 |
| GB | 2078763 A | 1/1982 |
| JP | 59-500046 A | 1/1984 |
| JP | 61-203020 A | 12/1986 |
| JP | 62-87624 A | 6/1987 |
| JP | 01-265967 A | 10/1988 |
| JP | 2-140948 A | 11/1990 |
| JP | 3-56429 U | 5/1991 |
| JP | 06-509966 A | 11/1994 |
| JP | 7-016258 A | 1/1995 |
| JP | 2001-265967 A | 9/2001 |
| JP | 1130927 S | 11/2001 |
| JP | 2002-512980 A | 5/2002 |
| JP | 2002-521139 A | 7/2002 |
| JP | 2002-537068 A | 11/2002 |
| JP | 2003-052741 A | 2/2003 |
| JP | 2003-153949 A | 5/2003 |
| JP | 58-124123 U | 1/2004 |
| JP | 2004-24905 A | 1/2004 |
| JP | 2006-061263 A | 3/2006 |
| JP | 2006-509966 A | 3/2006 |
| JP | 2007-522882 A | 8/2007 |
| JP | 3147394 U | 12/2008 |
| JP | 2009-022730 A | 2/2009 |
| JP | 1359502 S | 5/2009 |
| JP | 2011-004850 A | 1/2011 |
| JP | 1571238 S | 3/2017 |
| JP | 1629290 | 4/2019 |
| MX | 241113 A | 10/2006 |
| WO | WO 1983/002586 A | 8/1983 |
| WO | WO 1993/004650 A | 3/1993 |
| WO | WO 1995/004511 A | 2/1995 |
| WO | WO 1996/040797 A | 12/1996 |
| WO | WO 1998/026719 A | 6/1998 |
| WO | WO 2000/006213 A | 2/2000 |
| WO | WO 2000/049983 A | 8/2000 |
| WO | WO 2003/008002 A | 1/2003 |
| WO | WO 2004/049987 A | 6/2004 |
| WO | WO 2005/007020 A | 1/2005 |
| WO | WO 2005/051259 A | 6/2005 |
| WO | WO 2005/079674 A | 9/2005 |
| WO | WO 2006/017109 A | 2/2006 |
| WO | WO 2008/082444 A | 7/2008 |
| WO | WO 2009/067062 A | 5/2009 |
| WO | WO 2010/134873 A | 11/2010 |
| WO | WO 2011/152368 A1 | 12/2011 |
| WO | WO 2013/009725 A | 1/2013 |
| WO | WO 2014/083570 A | 6/2014 |
| WO | WO 2014/195710 A | 12/2014 |
| WO | WO 2015/135351 A | 9/2015 |

OTHER PUBLICATIONS

U.S. Appl. No. 15/452,126, filed Mar. 7, 2017, US-2017-0173208, U.S. Pat. No. 10,398,800, Sep. 3, 2019, Grant.
U.S. Appl. No. 15/467,537, filed Mar. 23, 2017, US-2018-0271712, U.S. Pat. No. 10,470,935, Nov. 12, 2019, Grant.
U.S. Appl. No. 15/490,176, filed Apr. 18, 2017, US-2017-0216482, U.S. Pat. No. 10,434,211, Oct. 8, 2019, Grant.
U.S. Appl. No. 15/496,389, filed Apr. 25, 2017, US-2018-0303967, Publication.
U.S. Appl. No. 15/675,159, filed Aug. 11, 2017, US-2018-0085260, U.S. Pat. No. 10,687,986, Jun. 2020, Grant.
U.S. Appl. No. 15/964,538, filed Apr. 27, 2018, US-2018-0243467, U.S. Pat. No. 10,398,802, Sep. 3, 2019, Grant.
U.S. Appl. No. 16/050,205, filed Jul. 2018, US-2020-0038006, U.S. Pat. No. 10,993,708, May 4, 2021, Grant.
U.S. Pat. No. 16/387,634, filed Apr. 18, 2019, US-2019-0240074, Publication.
U.S. Appl. No. 16/556,443, filed Aug. 30, 2019, US-2019-0381207, Publication.
U.S. Appl. No. 16/556,471, filed Aug. 30, 2019, US-2019-0381206, Publication.
U.S. Appl. No. 16/598,249, filed Oct. 10, 2019, US-2020-0038253, Publication.
U.S. Appl. No. 16/907,930, filed Jun. 22, 2020, US-2020-0315858, Publication.
U.S. Appl. No. 17/143,883, filed Jan. 7, 2021, US-2021-0121600, Publication.
U.S. Appl. No. 17/219,314, filed Mar. 2021, US-2021-0212676, Publication.
U.S. Appl. No. 29/503,320, filed Sep. 25, 2014, D. 824,525, Jul. 31, 2018, Grant.
U.S. Appl. No. 29/613,662, filed Aug. 11, 2017, D. 848,624, May 14, 2019, Grant.
U.S. Appl. No. 29/635,782, filed Feb. 2, 2018, Abandoned.
U.S. Appl. No. 29/648,487, filed May 22, 2018, D. 854,171, Jul. 16, 2019, Grant.
U.S. Appl. No. 29/683,074, filed Mar. 11, 2019, D. 907,217, Jan. 5, 2021, Grant.
U.S. Appl. No. filed May 13, 2019, Filing.
U.S. Appl. No. 29/761,282, filed Dec. 8, 2020, Filing.
JP 7040744, 1995, English claims.
JP 3059327, 1991, English claims.
Japanese Office Action dated Feb. 19, 2019 for Design Appln. No. 2018-017274.
Japanese Office Action dated Feb. 26, 2019 for Patent Appln. No. 515463.
3M™ Steri-Strip Adhesive Closures Product Catalog Brochure, (2011) 4 pages.
3M™ Steri-Strip Adhesive Closures Product Catalog Brochure, (2011) 8 pages.
3M™ Steri-Strip Adhesive Closures Product Catalog Brochure, (2012) 12 pages.
Allen, L.V. Jr et al. 'Ansel's Pharmaceutical Dosage Forms and Drug Delivery Systems, 8th edition 2005 Lippincott Williams & Wilkins, Chapter 4, Dosage Form Design: Pharmaceutical and Formulation Considerations p. 131.
Ashley et al.: Further studies involving wound closure with a rapidly polymerizing adhesive; *Plastic and Reconstructive Surgery*; Apr. 1963; vol. 31; pp. 333-343.
Ashley et al.: Nonsutured closure of skin lacerations and nonsutured grafting of skin with a rapidly polymerizing adhesive; *Qtrly Bull. Northwestern University (Evanston, Ill.) Medical School*; 1962; vol. 36; pp. 189-194.
Brombeg et al.: Nonsuture fixation of split-thickness skin grafts; *Surgery*, Jun. 1964; vol. 55; pp. 846-853.

(56) References Cited

OTHER PUBLICATIONS

Cramer: Rapid Skin Grafting in Small Animals; *Plastic and Reconstructive Surgery and the Transplantation Bull*; Oct. 1962, vol. 30; pp. 149-150.
Cramer et al.: Autograft rejection induced by homografting. A phenomenon intermediate between homograft rejection and autoimmunity; *Plastic and Reconstructive Surgery*; Jun. 1965; vol. 35; pp. 572-587.
DeMaria, E. 'New skin closure system facilitates wound healing after cardiovascular implantable electronic device surgery' World Journal of Clinical Cases (2015) 3(8) pp. 675-677.
Dermabond Prineo Skin Closure Systems (22 cm) Brochure (2014), 7 pages.
Dermabond Prineo Skin Closure Systems (22 cm) Brochure (2015), 2 pages.
Healthcare Packaging. Advanced Wound Care Products and packaging Needs. Jun. 5, 2017 (earliest online date), [site visited May 8, 2018]. Available from the Internet, URL:https://www.healthcarepackaging.com/article/applications/healthcare/advanced-wound-care-products-and-packaging-needs> (Year: 2017).
Inou: Studies on the Surgical Use of Plastic Adhesive; *Am. Journal of Proctology*; 1962; vol. 13; pp. 219-226.
Jesse et al.: Fixation of split-thickness skin grafts with adhesive; *Plastic and Reconstructive Surgery*; Mar. 1964; vol. 33; pp. 272-277.
Kaplan: A technique of nonsuture wound closure with a plastic tissue adhesive; *Plastic and Reconstructive Surgery*; Feb. 1966; vol. 37(2); pp. 139-142.
Keddie et al.: Intrafollicular tinea versicolor demonstrated on monomer plastic strips; *Journal of Investigative Dermatology*; Sep. 1963; vol. 41; pp. 103-106.
Lazar, H.L. et al. 'Novel Adhesive Skin Closures Improve Wound Healing Following Saphenous Vein Harvesting' J. Card Surg (2008) 23 pp. 152-155.
Leukosan SkinLink Application Guide (2006) 1 page.
Leukosan Skinlink. BSN Medical (2017) 1 page http://www.bsnmedical.com/products/wound%E2%80%90care%E2%80%90vascular/category%E2%80%90product%E2%80%90search/acute%E2%80%90wound%E2%80%90care/wound%E2%80%90closure/leukosanr%E2%80%90skinlink.html.
N/A, "Scar nose & Rinoplasty Surgery—New Gel+Demo:Nose Silicone Gel Sheet (beige)www.newgelplus.com", www.youtube.com, 2012, pp. 1-3.
N/A, "Silagen Silicone Sheeting Strips Review | the skin spot", www.youtube.com, 2017, pp. 1-3.
Pam Marketing Nut. Yikes! The Social Medica Quick Fix Band-Aids are Falling Off! Jul. 2012 [earliest online date], [site visited May 8, 2018]. Available from Internet, ,URL:http://www.pammarketingnut.com/2012/07/yikes-the-social-media-quick-fix-band-aids-are-falling-off/> (Year: 2012).
Parrish et al.: Synthetic resin adhesive for placement of skin grafts; *American Surgeon*; Nov. 1964; vol. 30; pp. 753-755.
Raekallio et al.: Acute reaction to arterial adhesive in healing skin wounds; *Journal of Surgical Research*; Mar. 1964; vol. 4; pp. 124-127.
Stone: Nonsuture closure of cutaneous lacerations, skin grafting and bowel anastomosis; *American Surgeon*; Mar. 1964; vol. 30; pp. 177-181.
TissuGlu Surgical Adhesive Patient Information Brochure. Cohera Medical, Inc. (2014) 6 pages.
TissuGlu FDA Summary of Safety and Effectiveness Data. Feb. 3, 2014 40 pages.
Topaz, M. et al. 'The TopClosure 3S System, for skin stretching and a secure wound closure' Eur J Plast Surg (2012) 35 pp. 533-543.
TopClosure 3S System—Skin Stretching and Secure Wound Closure System Product Information Sheet (2010) 15 pages.
Wang et al. 'Biodegradable microfluidic scaffolds for tissue engineering from amino alcohol-based poly(ester amide) elastomers' Organogenesis (2010) 6:4, pp. 212-216.

Wolfe et al.: The application of hydrostatic pressure to the burn injury, an experimental study: *Journal of Trauma: Injury Infections & critical Care*; May 1962; vol. 2; pp. 262-272.
ZipLine medical Zip Surgical Skin Closure Brochure (2013) 4 pages.
Corrected International Search Report International Application No. PCT/US2005/004948 dated Jun. 22, 2005.
Extended European Search Report re: 14166813.7 dated Jul. 7, 2014.
International Preliminary Report on Patentability for International Application No. PCT/US2005/024042 dated Jan. 16, 2007.
International Search Report for International Application No. PCT/US2005/024042 dated May 12, 2006.
International Search Report for International Application No. PCT/US2005/004948 dated Jun. 9, 2009.
International Search Report re: PCT/US2015/051919 dated Apr. 14, 2016.
International Search Report re: PCT/US2017/052394 dated Nov. 21, 2017.
International Search Report re: PCT/US2017/052383 dated Dec. 6, 2017.
International Search Report re PCT/US2018/022842 dated Jun. 20, 2018.
International Search Report re PCT/US2018/022834 dated Jun. 22, 2018.
International Search Report re PCT/US2018/027790 dated Jun. 26, 2018.
Supplementary European Search Report for Application No. EP05769387 dated Jul. 9, 2009.
Supplementary European Search Report for Application No. EP05723162 dated Nov. 5, 2009.
Supplementary European Search Report for Application No. EP14166813 dated Jun. 30, 2014.
Written Opinion re: PCT/US2015/051919 dated Apr. 14, 2016.
Written Opinion re: PCT/US2017/052394 dated Nov. 21, 2017.
Written Opinion re: PCT/US2017/052383 dated Dec. 6, 2017.
Written Opinion re: PCT/US2018/022842 dated Jun. 20, 2018.
Written Opinion re: PCT/US2018/027790 dated Jun. 26, 2018.
Written Opinion re PCT/US2018/022834 dated Jun. 22, 2018.
Communication received from the USPTO for co-pending U.S. Appl. No. 10/887,884 dated Aug. 11, 2006.
Communication received from USPTO for co-pending U.S. Appl. No. 10/779,721 dated Mar. 28, 2007.
Communication received from USPTO for co-pending U.S. Appl. No. 10/779,721 dated Apr. 16, 2007.
Communication received from the USPTO for co-pending U.S. Appl. No. 10/887,884 dated Mar. 6, 2008.
Communication received from the USPTO for co-pending U.S. Appl. No. 10/887,884 dated Dec. 12, 2008.
Communication received from the USPTO for co-pending U.S. Appl. No. 12/207,984 dated May 11, 2011.
Communication received from the USPTO for co-pending U.S. Appl. No. 12/163,021 dated May 13, 2011.
Communication received from the USPTO for co-pending U.S. Appl. No. 12/163,021 dated Feb. 2, 2012.
Communication received from the USPTO for co-pending U.S. Appl. No. 12/163,021 dated Jun. 22, 2012.
Communication received from the USPTO for co-pending U.S. Appl. No. 12/207,984 dated Jun. 28, 2012.
Communication received from USPTO for co-pending U.S. Appl. No. 12/163,021 dated Jun. 22, 2012.
In re the U.S. Appl. No. 12/163,021 the Non-Final rejection dated Aug. 14, 2013.
In re the U.S. Appl. No. 12/163,021 the Final rejection dated Jan. 3, 2014.
In re the U.S. Appl. No. 12/207,984 the Non-Final rejection dated Aug. 22, 2013.
In re the U.S. Appl. No. 12/207,984 the Final rejection dated Dec. 4, 2013.
Office action received from USPTO for co-pending U.S. Appl. No. 10/887,884 dated Apr. 25, 2006.
Office action received from USPTO for co-pending U.S. Appl. No. 10/779,721 dated Aug. 21, 2006.

(56) References Cited

OTHER PUBLICATIONS

Office action received from USPTO for co-pending U.S. Appl. No. 10/887,884 dated Oct. 12, 2006.
Office action received from USPTO for co-pending U.S. Appl. No. 10/779,721 dated Jan. 9, 2007.
Office Communication received from USPTO for co-pending U.S. Appl. No. 10/887,884 dated Jan. 22, 2007.
Office Action received from USPTO for co-pending U.S. Appl. No. 10/887,884 dated Feb. 1, 2007.
Office Action received from the USPTO for co-pending U.S. Appl. No. 12/163,021.
Office action received from USPTO for co-pending U.S. Appl. No. 10/779,721 dated Jul. 27, 2007.
Office Action received from USPTO for co-pending U.S. Appl. No. 10/887,884 dated Oct. 16, 2007.
Office Action received from USPTO for co-pending U.S. Appl. No. 10/887,884 dated Mar. 6, 2008.
Office action received from USPTO for co-pending U.S. Appl. No. 10/779,721 dated May 19, 2008.
Office action received from USPTO for co-pending U.S. Appl. No. 12/163,021 dated Jan. 9, 2010.
Office action received from USPTO for co-pending U.S. Appl. No. 12/163,021 dated Sep. 1, 2010.
Office action received from USPTO for co-pending U.S. Appl. No. 12/207,984 dated Sep. 1, 2010.
Office action received from USPTO for co-pending U.S. Appl. No. 12/163,021 dated Dec. 9, 2010.
Office action received from USPTO for co-pending U.S. Appl. No. 12/207,984 dated Dec. 9, 2010.
Office action received from USPTO for co-pending U.S. Appl. No. 12/163,021 dated May 13, 2011.
Office action received from USPTO for co-pending U.S. Appl. No. 12/163,021 dated Jul. 18, 2011.
Office action received from USPTO for co-pending U.S. Appl. No. 12/207,984 dated Aug. 1, 2011.
Office action received from USPTO for co-pending U.S. Appl. No. 12/163,021 dated Jan. 10, 2012.
Office action received from USPTO for co-pending U.S. Appl. No. 12/207,984 dated Jan. 17, 2012.
Office action received from USPTO for co-pending U.S. Appl. No. 12/207,984 dated Apr. 26, 2012.
Office action received from USPTO for co-pending U.S. Appl. No. 12/163,021 dated May 1, 2012.
Office action received from USPTO for co-pending U.S. Appl. No. 12/163,021 dated Sep. 17, 2012.
Office action received from USPTO for co-pending U.S. Appl. No. 12/207,984 dated Sep. 25, 2012.
Office action received from USPTO for co-pending U.S. Appl. No. 12/163,021 dated Aug. 14, 2013.
Office action received from USPTO for co-pending U.S. Appl. No. 12/207,984 dated Aug. 22, 2013.
Office action received from USPTO for co-pending U.S. Appl. No. 12/207,984 dated Dec. 4, 2013.
Office action received from USPTO for co-pending U.S. Appl. No. 12/163,021 dated Jan. 3, 2014.
Office action received from USPTO for U.S. Appl. No. 15/964,538 dated Oct. 25, 2018.
Office action received from USPTO for U.S. Appl. No. 15/964,538 dated Dec. 27, 2018.
Office action received from USPTO for U.S. Appl. No. 15/490,176 dated Feb. 4, 2019.
Office action received from USPTO for U.S. Appl. No. 15/452,126 dated Nov. 16, 2018.
Office action received from USPTO for U.S. Appl. No. 14/864,033 dated Nov. 26, 2018.
Office action received from USPTO for U.S. Appl. No. 15/467,239 dated Feb. 28, 2019.
Office action received from USPTO for U.S. Appl. No. 15/278,376 dated Sep. 11, 2018.
Office action received from USPTO for U.S. Appl. No. 15/278,376 dated Feb. 21, 2019.
Office action received from USPTO for U.S. Appl. No. 15/675,159 dated May 14, 2019.
U.S. Appl. No. 09/430,177, filed Oct. 29, 1999.
U.S. Appl. No. 09/430,289, filed Oct. 29, 1999.
U.S. Appl. No. 09/430,180, filed Oct. 29, 1999.
U.S. Appl. No. 09/385,030, filed Aug. 30, 1999.
U.S. Appl. No. 09/176,889, filed Oct. 22, 1998.
U.S. Appl. No. 09/919,877, filed Aug. 2, 2001.
U.S. Appl. No. 10/779,721, filed Feb. 18, 2004.

\* cited by examiner

ADHESIVE-CONTAINING WOUND CLOSURE DEVICE AND METHOD

BACKGROUND OF THE INVENTION

1. Field of Invention

The present invention relates to medical and surgical wound closure and management, and methods for making and using such devices. In particular, the present invention relates to medical and surgical wound closure and management, and related methods, where the tissue bonding article or wound closure device incorporates a polymerizable adhesive material applied to an initiator-loaded textile material. The materials and methods of the present invention provide an improvement over, and a substitute for, conventional bandages, sutures and staples, and provide improved methods for both approximating and covering and/or closing wounds, thus providing improved wound management.

2. Description of Related Art

There are currently in primary use at least four basic ways for closing wounds resulting from surgical incisions or accidental lacerations. These are sutures, surgical staples, surgical skin tapes, and adhesive compositions. Sutures are generally recognized as providing adequate wound support for the duration of wound healing. However, suturing involves additional trauma to the wound, as the needle and suture material must be passed through the tissue at the margins of the wound. In addition, suturing can cause cosmetically unattractive wound closure marks, can be time consuming, and, depending on techniques and types of sutures used, may require removal. Such removal entails further medical attention and can involve additional pain and trauma to the patient particularly if the sutures become embedded in the wound. In some cases, suture removal can require anesthetic, and can result in a railroad track appearance at the wound site.

Surgical staples have disadvantages similar to sutures in terms of cosmetic result. However, staples are generally believed to be even worse then sutures, at least in terms of the pain and trauma inflicted on the patient, and the resultant cosmetic appearance of the staple and wound marks. Further, removal of the staples can be painful and, depending on location and patient pain threshold, may require topical anesthetics.

Skin closure strips, such as conventional adhesive bandages, are utilized for closure of relatively superficial skin wounds, but their use is limited to only certain types and degrees of wounds. However, the contact adhesives that are used with such strips typically retain holding power for no more than a day or two and can lose holding power quickly in the presence of moisture, for example, perspiration.

Direct application of adhesives has also been proposed and used for wound closure purposes, especially involving cyanoacrylate adhesives. Such materials are achieving more widespread use for wound closure.

For example, monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of 1,1-disubstituted ethylene adhesive compositions include use as an alternate or an adjunct to surgical sutures and staples in wound closure as well as for covering and protecting surface wounds such as lacerations, abrasions, burns, stomatitis, sores, and other surface wounds. When an adhesive is applied, it is usually applied in its monomeric form, and the resultant polymerization gives rise to the desired adhesive bond.

For example, polymerizable 1,1-disubstituted ethylene monomers, and adhesive compositions comprising such monomers, are disclosed in U.S. Pat. No. 5,328,687 to Leung et al. Suitable methods for applying such compositions to substrates, and particularly in medical applications, are described in, for example, U.S. Pat. Nos. 5,582,834, 5,575,997, and 5,624,669, all to Leung et al.

Combinations of the above approaches have also been used in the art. For example, attempts have been made to combine the use of sutures or staples and adhesive compositions. See, for example, U.S. Pat. No. 5,254,132. Likewise, attempts have been made to combine the use of conventional bandages or tapes and adhesive compositions. See, for example, U.S. Pat. Nos. 5,259,835 and 5,445,597. However, these approaches have typically met the same issues as described above for the individual approaches, namely difficulties arising from the use of the sutures, staples and/or bandages or tapes.

Current approaches for combining the above wound closure approaches also include combining the use of adhesive compositions and bandage-like dressings. For example, U.S. Patent Publications Nos. 2002-0049503 and 2004-0106888 each disclose the combined use of adhesive compositions and mesh bandage-like materials. In each case, a mesh-like structure is applied to a wound, and an adhesive composition is applied to the mesh-like structure. When the adhesive composition sets, it bonds the mesh-like structure to the wound. In U.S. Patent Publication No. 2004-0106888, the wound dressing includes removable ends that adhere the mesh-like structure to the wound, but which can be removed after the adhesive composition sets, leaving the adherent dressing in place.

Commonly assigned U.S. patent application Ser. No. 10/779,721, filed Feb. 18, 2004, also discloses a combined adhesive composition and bandage-like dressing. The application discloses a tissue bonding article, comprising: a flexible material; an adhesive substance applied over at least a portion of a bottom side of said flexible material, for at least temporarily adhering the flexible material to a wound surface; and a polymerizable adhesive composition permeated throughout at least a portion of said flexible material. When the polymerizable adhesive polymerizes, the flexible material is adhered to the wound surface to provide an adherent composite dressing. The entire disclosure of this application is incorporated herein by reference.

A difficulty with these combined adhesive/flexible substrate approaches is in the application and polymerization of the adhesive composition. For example, where a polymerizable adhesive composition is applied to the substrate, the adhesive is either applied from an applicator device that includes a polymerization initiator, or the adhesive composition (which contains no initiator) is applied to the flexible substrate and wound site where polymerization is initiated by moisture or other fluids present at the wound site. In the first instance, polymerization of the adhesive composition is rapid, but the presence of the polymerization initiator in the applicator device creates a short working time, requiring that the adhesive composition be applied rather quickly. In the second instance, the working time of the adhesive composition is longer because the applicator device does not include a polymerization initiator. However, polymerization of the adhesive composition on the wound site is typically much longer and less consistent because polymerization relies upon weaker species (such as moisture or other natural substances present on the skin and not added specifically for polymerization initiation) that may be present in differing amounts.

Accordingly, a need continues to exist for improved materials and methods for wound approximation. A need also continues to exist for improved materials and methods that have a wider range of applications, from external to internal use, and from essentially non-biodegradable (where the materials are removed from the application site) to biodegradable (where the materials are not directly removed from the application site, but instead degrade over time).

SUMMARY OF THE INVENTION

The present invention addresses the above needs in the art, and others, by providing improved materials and methods for wound management, bonding, and approximation.

In embodiments, the materials and methods of the present invention provide significant advantages over the current materials and methods for wound closure. The materials and methods of the present invention can fully replace the use of bandages, sutures, and/or staples on a variety of wounds and tissue surfaces. These advantages include, among others, improved wound closure, improved wound approximation, provision of an improved durable microbial barrier, reduced procedure time, improved working time, improved cosmesis, less pain (during staple/suture removal) resulting in increased patient satisfaction, and improved financial/economic outcomes by eliminating follow-up visits for staple/suture removal.

In embodiments, the materials and methods of the present invention also provide significant advantages in terms of application of the wound closure device. In particular, because the flexible material is loaded with initiator for the subsequently applied polymerizable adhesive material, the polymerizable adhesive material rapidly and uniformly polymerizes on and in the flexible material to form an adherent device, but without unacceptably high heat generation. This faster set time (the time between application and substantial polymerization of the polymerizable adhesive material) means that wound closure can be quickly effected. Furthermore, because the flexible material is loaded with initiator for the subsequently applied polymerizable adhesive material, the polymerizable adhesive material does not need to be applied in a mixed state including initiator or through an applicator device that provides an initiator. As such, the working time (the time during which the polymerizable adhesive material can be applied before becoming polymerized in the applicator) is unlimited.

In an embodiment, the present invention provides an article, comprising: a flexible material; a polymerization initiator or rate modifier disposed in or on said flexible material; and a polymerizable adhesive composition permeated throughout at least a portion of said flexible material, wherein said polymerization initiator or rate modifier is a polymerization initiator or rate modifier for said polymerizable adhesive composition. The article can be a tissue bonding article for bonding tissue surfaces, or can be used in other applications.

In another embodiment, the present invention provides a method of bonding tissue, comprising: placing a flexible material over a substrate, wherein a polymerization initiator or rate modifier disposed in or on said flexible material; applying a polymerizable adhesive composition over and substantially covering at least a portion of the flexible material; and allowing the polymerizable adhesive composition to permeate into and under the flexible material and polymerize to form a composite structure bonded to said substrate.

The composite structures of the present invention, when used as tissue bonding articles, can be used to bond a variety of tissue ranging from hard tissue (such as bone) to soft tissue (such as skin, organs, mucous membranes, and the like). The tissue can be either internal or external.

DETAILED DESCRIPTION OF PREFERRED EMBODIMENTS

In embodiments, the present invention provides wound closure devices and methods, that provide some or all of the above advantages. The present invention provides such benefits by providing, as a wound closure device, a flexible material that can be applied to a surface, and impregnated with a polymerizable monomeric adhesive composition, which upon setting or curing provides an adherent structure over the surface. Polymerization (setting or curing) of the polymerizable monomeric adhesive composition is assisted by the flexible material being loaded, coated, or the like with a polymerization initiator or rate modifier for the polymerizable monomeric adhesive composition.

In embodiments, the flexible or compliant material can be formed of any suitable flexible or compliant material, providing that the aims of the present invention are obtained. Preferably, the flexible or compliant material is a material that is flexible, porous, and non-toxic. As used herein, the term "flexible" is used to refer to the flexible or compliant material. However, unless stated differently in context, the term "flexible" is meant to cover a range of materials, which exhibit one or more properties such as being flexible, compliant, elastic, or memory retentive. For example, "flexible" is also meant to refer to materials that exhibit elastic or memory properties, i.e., the ability for the material to return to its original shape when stresses applied thereto are reduced or eliminated.

The flexible material is preferably flexible or compliant, to allow the flexible substrate to be placed on the desired surface (such as skin, organ, tissue, or the like) in a manner that allows the flexible substrate to conform to the topology of the desired surface. Likewise, the flexible material is preferably porous, to allow the subsequently applied polymerizable adhesive material to pass through or permeate through the flexible material and to polymerize as a layer beneath the flexible material, while adhering the flexible material to the desired substrate. By "porous" is meant herein either that the bulk of the flexible material has pores, such that the subsequently applied polymerizable adhesive material is soaked up or absorbed by the bulk material, or that the bulk of the flexible material has voids (like a net or screen), such that the subsequently applied polymerizable adhesive material passes directly through the bulk material, with or without being soaked up or absorbed by the bulk material. For example, in the case of textile materials, "porous" is generally used to mean that the applied adhesive composition permeates and passes through interstices between the fibers, but does not necessarily pass into and through the fibers themselves.

Such porosity (or other properties such as hydrophobicity or hydrophilicity) will also allow a polymerization initiator or rate modifier to be loaded on the flexible material prior to use, to initiate the subsequently applied polymerizable adhesive material. Such porosity will also preferably allow air and water to pass through the flexible material (either through pores per se, or through voids in the bulk material). Depending upon the degree of porosity (and/or the size of the openings in the textile), such porosity of the flexible material or ability of air and water to permeate through the flexible material may be tailored to either remain after the final composite material is formed, or to be absent therefrom. The flexible material is also preferably non-toxic, as it is intended to be used as a wound covering, such as on biological tissues. As such, the flexible material should be biologically compatible with the desired substrate (such as tissue, skin, organ, or the like), and is preferably a material that is governmentally approved or generally regarded as safe for the desired purpose.

In other embodiments, the flexible material may be selected to be elastic or have some memory effect. In such embodiments, the elastic properties of the flexible material may desirably provide a degree of pressure or stress at the application site, for example, to maintain wound edge approximation. Likewise, in embodiments where such additional degree of pressure or stress at the application site is not desired, the flexible material may be selected to have less or no elasticity.

In embodiments of the present invention, the flexible material can be either biodegradable, or not biodegradable. "Biodegradable" in this invention is meant that the flexible substrate biodegrades over time in vivo, such that it does not require physical removal (such as by peeling) of the composite structure after a set period of time. Thus, for example, a biodegradable flexible material is one that, in the in vivo environment, will biodegrade over a period of from about one week to about five years. A non biodegradable material is one that does not biodegrade in an in vivo environment within about five years. Such a non biodegradable material thus would require physical removal of the composite structure at a desired time, rather than slowly deteriorating over time. Likewise, in some embodiments, it is preferred that the combination of materials forming the composite structure (i.e., the flexible material and the polymerizable adhesive composition) together be biodegradable, while in other embodiments, it is preferred that the combination of materials forming the composite structure (i.e., the flexible material and the polymerizable adhesive composition) together be not biodegradable. Biodegradable and non-biodegradable polymerizable adhesive compositions are known in the art and are described below. Alternatively, combination of two or more biodegradable and/or non-biodegradable materials can be used, to provide tailored results in terms of properties such as biodegradation and the like.

For biodegradable materials, a range of materials can be selected as the flexible material, preferably to provide a desired target biodegradation time. Thus, for example, suitable materials can be selected to provide either a short biodegradation period (such as between about one week and about two months) or a longer biodegradation period (such as between about two months and about five years). Suitable selection of the flexible material will thus allow tailoring of the flexible substrate to the particular application. For example, in embodiments where the flexible substrate is used to form a composite structure on the surface of a patient's skin (such as in the conventional context of a bandage), it is desirable that the flexible substrate is not biodegradable. Rather, after a set period of time, the composite structure is physically removed (such as by peeling, by the use of a chemical removal substance to break the adhesive bond, or by natural sloughing off of the composite structure with the surface skin), either to permit completion of healing or to reapply a new composite structure. Such removal of the composite structure from the tissue surface is easier than removal of a layer of polymerizable adhesive composition alone. In other embodiments, however, it may be desirable that the composite structure biodegrade over a set period of time, for example when the composite structure is used internally where subsequent removal would otherwise require further trauma to the tissue.

In embodiments, it is preferred that the flexible material is a textile or mesh/web material. Suitable textile materials can be formed of either synthetic or natural materials. Such textile material can be formed of either woven or non-woven fabrics or materials. The flexible material may be, for example, any suitable polymeric film, plastic foam (including open celled foam), a woven fabric, knitted fabric, a non-woven fabric, mixture thereof, or the like. In particular, suitable flexible materials may thus be prepared, for example, from nylon, a polyolefin film, such as polyethylene, polypropylene, ethylene propylene copolymers, and ethylene butylene copolymers, polyurethanes, polyurethane foams, polystyrenes, plasticized polyvinylchlorides, polyesters, polyamides, and cotton. Suitable specific examples include, for example, nylon, polyethylene, polypropylene, ethylene propylene copolymers, ethylene butylene copolymers, polyurethane, polystyrene, plasticized polyvinylchloride, polyester, polyamide, cotton, polytetrafluoroethylene (PTFE), biovascular material, collagen, Gore-Tex®, DACRON®, etc.

In some embodiments, it is preferred that the textile material not be formed of elastin, or elastin-based materials. Although elastin may be suitable for some uses, synthetic materials are preferred in embodiments in view of their availability, ease of manufacture, physical properties such as strength and durability, and biological compatibility. Thus, in such embodiments, it is preferred that the textile material is substantially or completely free of elastin or elastin-based materials. Further, in such embodiments, it is preferred that the entire flexible substrate (i.e., the combination of the flexible material and the adhesive substance) is substantially or completely free of elastin or elastin-based materials.

In other embodiments, it is preferred that the flexible material be formed of a synthetic, semi-synthetic, or natural organic material. Thus, for example, it is preferred that the flexible material be formed of a synthetic or natural polymer material, but not from a material such as metal (such as silver, steel or the like) or glass or ceramic.

The flexible material is preferably flexible, as described above, yet resistant to tearing. In one embodiment, the thickness of the flexible material of the present invention is from about 0.1 mil to about 50 mils. In another embodiment, the thickness of the flexible material is from about 0.5 mil to about 20 mils, preferably from about 0.7 mil to about 10 mils, or from about 1 mil to about 5 mils.

The flexible material may be opaque or translucent. In some embodiments of the present invention, the flexible material is provided to have a skin color, such that the flexible material masks the appearance of the underlying surface (such as a wound). However, in other embodiments, the flexible material can be provided with "designer" colors and/or patterns, or even cartoon character designs. In other embodiments, the flexible material may be clear, thus not masking the underlying surface.

In some embodiments, the flexible material can include a pressure sensitive adhesive on at least one face, to assist in initial placement of the flexible material on the desired surface. However, in other embodiments, the flexible material preferably does not include such pressure sensitive adhesive on one or both sides, as such pressure sensitive adhesive can hinder subsequent attachment of the flexible material to the surface by the polymerizable adhesive composition.

In embodiments where the flexible material includes a pressure sensitive adhesive applied to portions of the flexible material, the pressure sensitive adhesive can be applied to an entire surface of the flexible material, or only to portions (such as peripheral edges) of the surface of the flexible material. The exposed pressure sensitive adhesive can be covered by a suitable release layer or liner, if desired, to preserve the adhesiveness of the flexible material until time of use. The pressure sensitive adhesive, if present, can be applied in the various manners shown in U.S. patent application Ser. No. 10/779,721, the entire disclosure of which is incorporated herein by reference.

The size of the flexible material can be tailored for specific intended uses, or it can be provided in a sheet or roll form. Thus, for example, when forming a rectangular composite for use in the present invention, any suitable dimensions of the flexible material can be provided. For example, in the conventional bandage configuration, the flexible material can range in width from about ¼ inch to about 2 or 3 inches or more, although preferred widths in embodiments may be from about ½ to about 1 or 1½ inches, and can range in length from about ½ inch to about 4 or 5 inches or more, although preferred lengths in embodiments may be from about 1 to about 2 or 3 inches. Likewise, in the configuration of being a lengthwise bandage or rolled tape, such as to be used to cover lengthwise wounds or surfaces, the flexible material can range in width from about ½ inch to about 4 or 5 inches or more, although preferred widths in embodiments may be from about 1 to about 2 or 3 inches, and can range in length from about 1 inch to about 6 or 8 inches or more, although preferred lengths in embodiments may be from about 2 to about 4 or 5 inches. However, a particular advantage of this embodiment is that the flexible material may be used to form a composite structure over a longer wound, such as a long laceration on incision. As such, embodiments of the present invention can provide a flexible material having a length exceeding 8 or even 12 inches, such as ranging in lengths up to 18 inches, 24 inches, 30 inches, or more. When provided in the configuration of a roll, the flexible material can have virtually any practical length, such as 5, 6, 8, 10, or 12 feet or more, which can be cut to desired length at the time of use. Of course, it will be apparent that the materials of the present invention are not limited to any particular dimensions, and that the dimensions (length, width, thickness, etc.) of the flexible material can be varied and tailored, as desired.

As such, various sized flexible materials can be prepared and packaged for use. For example, shorter length materials (for example, in lengths up to about 2, 3 or 4 inches) can be prepared and packaged for use in "short laceration" applications, while longer length materials (for example, in lengths up to about 10, 15, 20 or 30 inches) can be prepared and packaged for use in "long laceration" applications. In other embodiments, a variety of length materials can be provided, with the intention that the materials are single use materials; where any leftover length of the flexible material is discarded. Such single-use embodiments are particularly desirable where the flexible material is sterilized, and sterility is desired to be maintained until the time of use. In other embodiments, such as where sterility is not a requirement, a longer length of flexible material can be provided where any unused portion can be saved for later use.

Still other configurations for the flexible material will be apparent to those skilled in the art. For example, although described above as being in rectangular or square configurations, the flexible substrate can take any number of other shapes, which can be designed for particular applications. For example, circular or round (disc-shaped) flexible materials can be used, such as to cover blister bases, sores, or the like; arc-shaped (curved rectangular shaped) flexible materials can be used, such as to cover curved lacerations or incisions; and the like. Other shapes, such as oval, triangular, polygonal, semi-circular, and the like, can also be used, in embodiments.

Preferably, the flexible material does not include additional structures for attaching the flexible material to the desired application or treatment site. Thus, for example, the flexible material does not further include other physical attachment means such as hooks, barbs, pins, projections, or the like, which operate to physically latch or otherwise attach the flexible substrate to the desired application or treatment site. Such attachment means are not desired, for example, because they introduce additional trauma to the underlying surface. Thus, it is preferred that the flexible material not include features that penetrate even surface layers of the underlying substrate, such as dermal layers of the skin.

According to the present invention, the flexible material includes one or more chemical materials located within the flexible material. For example, one or more chemical substances can be dispersed in the flexible material, such as being chemically bound, physically bound, absorbed, or adsorbed to the flexible material. Thus, for example, the flexible material includes at least a polymerization initiator or rate modifier, and can optionally include one or more bioactive materials. As desired, the one or more chemical substances can be either immobilized on the flexible material, for example so that it has a desired effect but is not detached from the flexible material during use, or it can be attached to the flexible material in a manner such that it becomes detached during use.

For example, according to the present invention, a polymerization initiator or rate modifier is loaded on the flexible material, so that the initiator or rate modifier provides the desired initiation or rate modification effect to a subsequently applied polymerizable adhesive composition. The polymerization initiator or rate modifier can be immobilized on the flexible material, so that the initiator or rate modifier does not become detached from the flexible material and its residues dispersed in the resultant polymeric material. Alternatively, for example, the polymerization initiator or rate modifier may be initially attached to the flexible material, but only in such a manner that it becomes mobilized or solubilized by a subsequently applied polymerizable adhesive composition and dispersed in the resultant polymeric material.

If desired, a combination of chemical substances can also be provided on the flexible material, to provide multiple effects. For example, as described above, a first chemical species (such as a polymerization initiator or rate modifier) can be immobilized on the flexible material, while a second, different chemical species (such as a bioactive material) can be detachably attached to the flexible material. Other combinations of chemical species and resultant effects are also envisioned by the present invention.

When present in or on the flexible material, the chemical substances (i.e., polymerization initiator, rate modifier, and/or bioactive materials, or other additives), can be incorporated in or on the flexible material in any suitable manner. For example, the chemical substance can be added to the flexible material by contacting the flexible material with a solution, mixture, or the like including the chemical substances. The chemical substance can be added to the flexible material, for example, by dipping, spraying, roll coating, gravure coating, brushing, vapor deposition, or the like. Alternatively, the chemical substance can be incorporated into or onto the flexible material during manufacture of the flexible material, such as during molding or the like of the flexible material.

The chemical substance can be present in or on the flexible material in any suitable concentration and manner. For example, the chemical substance can be applied in a uniform manner to the flexible material, such that there is a substantially uniform concentration of the chemical substance across the flexible material. Alternatively, the chemical substance can be applied such that a concentration gradient exists across or through the flexible material. For example, a greater or smaller concentration of the chemical substance could exist at the center or edges of the flexible material, or a greater or smaller concentration of the chemical substance could be applied on one side of the flexible material as compared to an opposite side. Further, the chemical substance can be applied in a uniform manner to the flexible substrate, or it can be applied in a non-uniform random or patterned manner (such as lines, dots, concentric circles, or the like).

Other chemical substances that can be present in or on the flexible material include, but are not limited to, any suitable and preferably compatible additive that enhances performance of the composite structure. Such additional chemical substances can be bioactive or non-bioactive. Suitable other chemical substances thus include, but are not limited to, colorants (such as inks, dyes and pigments), scents, protective coatings that do not chemically detach, temperature sensitive agents, drugs, and the like.

The present invention, by virtue of the polymerization initiator or rate modifier being loaded on the flexible material, provides a number of advantages over the prior art. For example, the structure of the present invention, in embodiments, allows for tailoring of the setting or polymerization time of the applied polymerizable adhesive composition. For example, as is well known in the art, the type and/or concentration of initiator that is applied to the flexible material can be selected so as to provide faster or slower polymerization time. For example, the concentration of polymerization initiator or rate modifier can be increased to provide a faster polymerization time, or can be decreased to provide a slower polymerization time.

Other properties of the polymerization can also be adjusted, in embodiments. For example, the polymerization can be made more uniform than previously possible, at least because the polymerization initiator or rate modifier is generally more uniformly applied to the flexible material. The cure temperature of the polymerizable adhesive composition can also be more easily tailored. For example, the initiator type and/or concentration can be selected to provide a desired polymerization or set time, while not generating excessive heat that could damage the underlying application surface.

These embodiments are preferred over at least some embodiments of the prior art. In the prior art, one method of applying a polymerizable adhesive composition was to apply the polymerizable adhesive composition to a substrate, and allow polymerization to be initiated by moisture of other species that may naturally be present. This often created long polymerization or set times, and led to undesirable results. For example, if tissue surfaces were being joined, the tissue surfaces would need to be physically held in place longer while the slow polymerization progressed, to avoid the wound from being opened. In such methods, polymerization time often varied from use to use, and thus was less reliable.

The present invention also provides, in embodiments, a longer working time for the polymerizable adhesive composition that is being used. Because the polymerization initiator or rate modifier is loaded directly on the flexible material, it is not necessary to mix the polymerizable adhesive composition with a polymerization initiator or rate modifier in an applicator prior to application. Thus, the applicator of the polymerizable adhesive composition does not suffer from the drawback of becoming plugged and unuseable as polymerizable adhesive composition polymerizes in an applicator tip. This can allow a longer working time, where the polymerizable monomer composition can be more precisely and carefully applied over a longer period of time.

These embodiments are thus likewise preferred over at least some other embodiments of the prior art. In the prior art, another method of applying a polymerizable adhesive composition was to apply the polymerizable adhesive composition through a porous applicator tip. The porous applicator tip is loaded with polymerization initiator or rate modifier, such that the polymerizable adhesive composition and polymerization initiator or rate modifier mix in the applicator tip. A drawback is that because the materials mix in the applicator tip, polymerization starts in the applicator tip. Accordingly, material within the applicator tip begins to polymerize, and can rapidly plug or clog the applicator tip, rendering the applicator and any further polymerizable adhesive composition contained therein unuseable. Such embodiments accordingly required faster use of the adhesive composition, and higher waste of adhesive composition.

In other embodiments, the present invention also provides still further operational advantages. For example, because the textile material tends to trap or act as a barrier to flow of the polymerizable adhesive composition, there is less running of the adhesive composition away from the application site. In addition, where one or more chemical substances are present in or on the textile, such chemical substances can be more specifically or precisely applied to the textile. For example, the chemical substances can be applied to the textile material only at specific locations, or in a gradient pattern, if desired. In these and other embodiments, the present invention provides a stronger composite structure than is provided by a polymerizable adhesive composition alone.

The above advantages, alone or in combination, can be provided by various embodiments of the present invention.

A method for using the flexible substrate and resultant composite structure will now be described.

The materials of the present invention are advantageously used as wound dressings. For example, the materials of the present invention are advantageously used as replacements for conventional bandages, or as replacements for conventional use of sutures and staples for closing wounds. As compared to conventional bandages, the flexible material of the present invention generally provides the same wound approximation and pressure benefits. However, because the flexible material is used to provide a composite structure by the addition of a polymerizable adhesive composition, the resultant composite structure provides significant benefits over the conventional bandage in terms of improved wound management, stronger adhesion to the underlying application site, microbial barrier properties, improved patient satisfaction, and the like. According to embodiments of the present invention, a polymerizable adhesive material is applied to the upper surface of the flexible material, which subsequently permeates through the flexible material (or at least through openings such as voids or pores in the flexible material) as the adhesive polymerizes, to form a flexible, adherent wound dressing. If desired, a first amount of a polymerizable adhesive material can be applied to the application site prior to applying the flexible material. The result is a unitary composite structure over the wound. Furthermore, as compared to conventional sutures and staples, the composite structure of the present invention also generally provides the same wound approximation and pressure benefits. However, because the composite structure uses a polymerizable adhesive composition rather than punctures for adhesion to the underlying application site, the resultant composite structure provides significant benefits over the conventional sutures and staples in terms of improved wound management, stronger adhesion to the underlying application site, microbial barrier properties, improved patient satisfaction, less tissue trauma (since additional punctures are not made), lessened scarring, and the like.

The materials of the present invention can also be advantageously used in non-medical or non-healthcare settings. For example, the materials of the present invention can also advantageously be used in commercial or household settings, where the flexible material/polymerizable adhesive composition composite structure can be used to provide stronger adhesion.

One method according to the present invention is described below. The method is described with reference to closing and covering a wound on a tissue surface. However, the invention is not limited to this embodiment.

In a first step, the application site, such as a wound or the like, is preferably cleaned by removing excess exudates (blood or the like) to provide as dry a wound as possible to assist in wound closure.

In a second step, a portion of flexible material is provided. Preferably, the length and width of the flexible material is longer and wider than the wound to be closed, and extend beyond opposite ends of the wound a sufficient distance to permit sufficient bonding. Thus, for example, the length of flexible material is preferably sufficient to extend at least ¼ inch, more preferably at least ½ inch or at least ¾, inch, and even more preferably at least one inch beyond each end of the wound. Furthermore, the flexible material is preferably wide enough to extend beyond each lateral edge of the wound throughout the length of the wound. The width of the flexible material is preferably wide enough that the entire wound is covered, with excess coverage, by the flexible material. That is, the flexible material preferably covers the full width of the wound, and extends beyond opposite lateral edges of the wound a sufficient distance to permit sufficient bonding. Thus, for example, the width of flexible material is preferably sufficient to extend at least ¼ inch, more preferably at least ½ inch or at least ¾ inch, and even more preferably at least one inch beyond each lateral edge of the wound.

In the second step, the flexible material is applied over the wound or desired surface. For ease of application, the surface is preferably horizontal, to help avoid slipping of the flexible material from the application site prior to complete polymerization of the subsequently applied polymerizable adhesive composition. However, where horizontal application is not possible or practical, the flexible material can be held in place by any suitable means including, but not limited to, by hand, forceps, tape, pressure sensitive adhesive, pressure, vacuum, or the like.

In a modification of this application method, a portion of a polymerizable adhesive material is applied to the application site prior to applying the flexible material. When so applied, the polymerizable adhesive material is preferably not allowed to fully polymerize prior to application of the flexible material and subsequent application of further amounts of polymerizable adhesive material. The polymerizable adhesive material applied prior to application of the flexible material can be the same as or different from the polymerizable adhesive material subsequently applied to the flexible material.

In a third step, a polymerizable adhesive composition, such as a polymerizable monomeric adhesive composition, is applied over at least a portion of the surface of the flexible material. Preferably, the polymerizable adhesive composition is applied to fully cover the surface of the flexible material. However, if desired, a lesser amount of the polymerizable adhesive composition can be used to conserve materials and assist in subsequent removal. For example, if a portion of the flexible material is not covered by the polymerizable adhesive composition, that portion can be used either to maintain control over the flexible material during placement and polymerization, and then subsequently trimmed off, or it can be maintained and used as a tab to assist in subsequent removal (such as by sloughing off or peeling off of the composite structure, or by the use of a remover substance). In this instance, the polymerizable adhesive composition is preferably applied to the flexible material at least in an area sufficient to cover the underlying wound or substrate.

In this step of applying the polymerizable adhesive composition, a sufficient amount of polymerizable adhesive composition should be applied to form the desired composite structure once the polymerizable adhesive composition has polymerized (or cured). Thus, for example, the amount of polymerizable adhesive composition should be sufficient to preferably allow the composition to penetrate through the flexible material to form a continuous coating between the flexible material and substrate, which continuous coating subsequently polymerizes or cures to form a continuous polymeric coating between the flexible substrate and the underlying surface. The quantity of polymerizable adhesive composition should preferably further allow for a quantity of the composition to remain in, and preferably over, the flexible material. This further amount of polymerizable adhesive composition polymerizes or cures with the remaining polymerizable adhesive composition to provide a unitary composite structure that is bonded to the underlying surface.

If necessary or desired, the step of applying polymerizable adhesive composition to the flexible material can be repeated one or more times. Thus, for example, a second or subsequent coating of the polymerizable adhesive composition can be applied, either prior or subsequent to complete curing of the underlying layer of polymerizable adhesive composition. Preferably, where multiple layers are to be applied, it is preferred that subsequent layers be applied after curing of the underlying layer has begun, but before curing is complete. If desired or necessary, subsequent layers of polymerizable adhesive material can be applied with an added polymerization initiator or rate modifier, to assist in polymerization of the adhesive composition.

As appropriate, the polymerizable adhesive composition can be applied to the flexible material either in the form of a continuous coating, or as discrete dots or dabs. For example, the discrete dots or dabs can be used either where the polymerizable adhesive composition is of high viscosity, and it is desired that the composite structure retain such discrete areas of adhesion, or where the polymerizable adhesive composition is of low viscosity such that the discrete dots or dabs will readily flow to form a continuous coating. A continuous coating can be assisted, for example, by spreading the applied polymerizable adhesive composition to any extent necessary.

However, if a continuous coating is desired when applying the polymerizable adhesive composition to the flexible material, the polymerizable adhesive composition is preferably applied over an entire surface of the flexible material. That is, while the flexible material may provide some wicking, flowing, or capillary movement of the polymerizable adhesive composition within the bulk material of the flexible substrate, such wicking or capillary movement is minimal, and is not intended to provide complete coverage of the polymerizable adhesive composition over the flexible material. Thus, for example, it will generally not be possible to apply one or two drops of the polymerizable adhesive composition to the flexible material, and expect the polymerizable adhesive composition to completely cover the flexible material (unless, of course, the flexible material is such a small size that the drops substantially cover the surface). Rather, in embodiments of the present invention, the polymerizable adhesive composition is applied by dabbing, brushing, rolling, painting, swabbing or the like, the polymerizable adhesive composition onto the flexible material. If necessary, the applied polymerizable adhesive composition can be spread around on the surface of the flexible material to provide improved coverage.

Once the polymerizable adhesive composition is cured, it forms a composite structure with the flexible material, covering the desired surface. The composite structure is adherent to the underlying surface, and provides the benefits described above.

Of course, although the invention is described with respect to the above application method, other methods will be readily apparent to those skilled in the art. The application methods are in no way limited to the methods described above.

As described above, one or more additives may be applied to the flexible substrate, which can subsequently chemically or physically interact with an applied polymerizable adhesive composition. Such chemical substances can include, for example, one or more polymerization initiators or rate modifiers, one or more additive materials, combinations thereof, and the like. According to the present invention, in embodiments, the flexible material is at least loaded or impregnated with one or more polymerization initiators or rate modifiers, as described above, to provide polymerization initiation to the subsequently applied polymerizable adhesive composition.

Suitable polymerization and/or cross-linking initiators and rate modifiers, and methods for applying them to substrates, are described in, for example, U.S. Pat. Nos. 5,928,611, 6,352,704, 6,455,064, 6,579,469 and 6,595,940 and U.S. patent application Ser. No. 09/430,177, filed Oct. 29, 1999, Ser. No. 09/430,289; 09/385,030 filed Aug. 30, 1999; and Ser. No. 09/176,889 filed Oct. 22, 1998, the entire disclosures of which are incorporated herein by reference. Preferred initiators for some medical uses include benzalkonium chloride, benzyldimethylhexa-decylammonium chloride, and for some industrial uses include dimethyl toluidine.

Particular initiators and rate modifiers for particular monomers may be readily selected by one of skill in the art without undue experimentation. Control of the molecular weight distribution of the applied adhesive can be enhanced by selection of the concentration and functionality of the initiator or rate modifier vis-a-vis the selected monomer. Suitable polymerization initiators and rate modifiers for cyanoacrylate compositions include, but are not limited to, detergent compositions; surfactants, including nonionic surfactants such as polysorbate 20 product (e.g., Tween 20™ product; ICI Americas), polysorbate 80 product (e.g., Tween 80™ product; ICI Americas), and poloxamers; cationic surfactants such as tetrabutylammonium bromide; anionic surfactants, including quaternary ammonium halides such as benzalkonium chloride or its pure components, and benzethonium chloride; stannous octoate (tin (II) 2-ethylhexanoate), and sodium tetradecyl sulfate; and amphoteric or zwitterionic surfactants such as dodecyldimethyl(3-sulfopropyl) ammonium hydroxide, inner salt; amines, imines, and amides, such as imidazole, tryptamine, urea, arginine and povidine; phosphines, phosphites and phosphonium salts, such as triphenylphosphine and triethyl phosphite; alcohols such as ethylene glycol; methyl gallate; ascorbic acid; tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat™ 336 (General Mills, Inc., Minneapolis, Minn.); organometallics; manganese acetylacetonate; radical initiators and radicals, such as di-t-butyl peroxide and azobisisobutyronitrile; and bioactive compounds or agents.

In preferred embodiments, the initiator may be a bioactive material (i.e., a material that affects a surrounding biological environment in addition to acting as a polymerization initiator), including quaternary ammonium halides such as alkylbenzyldimethylammonium chloride (benzalkonium chloride; BAC) its pure components, or mixtures thereof, especially those with an alkyl containing 6-18 carbon atoms; benzethonium chloride; and salts of sulfadiazine. Cobalt naphthenate can be used as an accelerator for peroxide.

In preferred embodiments, the initiator may also be a bioactive material that possesses antiviral, antimicrobial, antifungal and/or wound healing properties. An example of such a material that possesses polymerization initiation and antiviral, antimicrobial, and/or antifungal properties is Gentian Violet, also known as crystal violet or methylrosaniline chloride. Examples of materials that possess polymerization initiation and wound healing properties also include various zinc complexes and zinc salts, antioxidants such as vitamin E and other vitamins and the like, and copper compounds such as copper chloride, copper sulfate and copper peptides. Such materials are particularly preferred because they can serve not only as the polymerization initiator or rate modifier for the cyanoacrylate monomer, they can also provide additional benefits to the wound site, such as antiviral effects, antimicrobial effects and/or antifungal effects or help to promote wound healing.

When zinc compounds are present, the zinc compound can be present in various forms, such as zinc salts. For example, suitable zinc compounds include, but are not limited to, zinc salts of cyanoacrylic acid, zinc salts of cyanoacetic acid, zinc salts of dicyanoglutaric acid, zinc salts of rosin, zinc oxide, zinc salts of polycyanoacrylic acid, zinc salts of polyacrylic acid, zinc bacitracin, zinc salicylate, zinc stearate, zinc citrate, zinc lactate, mixtures thereof, and the like. Preferably, the zinc compounds are of $Zn^{2+}$. Incorporation of such zinc compounds into the polymerizable adhesive composition is particularly effective in promoting wound healing of leg ulcers, thermal burns, and the like.

The polymerizable adhesive composition and/or the flexible material may also contain an initiator and/or a rate modifier which is inactive until activated by a catalyst or accelerator (included within the scope of the term "initiator" as used herein). Initiators activated by stimulation such as heat and/or light (e.g., ultraviolet or visible light) are also suitable if the flexible material is appropriately subjected to such stimulation.

In addition to the polymerization and/or cross-linking initiator and/or rate modifier, the flexible material can also include various other materials that may or may not act as a polymerization initiator and/or rate modifier. For example, the flexible material can include a bioactive material, which may or may not also be a polymerization and/or cross-linking initiator and/or rate modifier. Thus, in embodiments, the initiator and/or the rate modifier can be, but does not have to be, bioactive. In embodiments where the initiator and/or the rate modifier is bioactive, the method of the invention can be used to close, cover, or protect tissue and wounds while simultaneously providing a bioactive material to the tissue or wound.

Suitable bioactive materials include, but are not limited to, medicaments such as antibiotics, antimicrobials, antiseptics, bacteriocins, bacteriostats, disinfectants, steroids, anesthetics, antifungal agents, anti-inflammatory agents, antibacterial agents, antiviral agents, antitumor agents, growth promoting substances, antioxidants, or mixtures thereof. Such compounds include, but are not limited to, acetic acid, aluminum acetate, bacitracin, bacitracin zinc, benzalkonium chloride, benzethonium chloride, betadine, calcium chloroplatinate, certrimide, cloramine T, chlorhexidine phosphanilate, chlorhexidine, chlorhexidine sulfate, chloropenidine, chloroplatinatic acid, ciprofloxacin, clindamycin, clioquinol, cysostaphin, gentamicin sulfate, hydrogen peroxide, iodinated polyvinylidone, iodine, iodophor, minocycline, mupirocin, neomycin, neomycin sulfate, nitrofurazone, non-onynol 9, potassium permanganate, penicillin, polymycin, polymycin B, polymyxin, polymyxin B sulfate, polyvinylpyrrolidone iodine, povidone iodine, 8-hydroxyquinoline, quinolone thioureas, rifampin, rifamycin, copper chloride, copper sulfate, copper peptides, silver acetate, silver benzoate, silver carbonate, silver chloride, silver citrate, silver iodide, silver nitrate, silver oxide, silver sulfate, sodium chloroplatinate, sodium hypochlorite, sphingolipids, tetracycline, zinc oxide, salts of sulfadiazine (such as silver, sodium, and zinc), antioxidants such as vitamins such as vitamin E, other agents mentioned above, and mixtures thereof. Preferable bioactive materials are USP approved, more preferably USP monographed.

As described above, the polymerization and/or cross-linking initiator and/or rate modifier, and/or the bioactive material, may be applied to the flexible material by any suitable means, including, but not limited to, spraying, dipping, injecting, or brushing the flexible material with a liquid medium containing the material to be applied.

As also described above, the composite structure is formed by applying a polymerizable adhesive composition to the flexible material, and allowing the polymerizable adhesive composition to polymerize. Polymerization of the polymerizable adhesive composition is initiated, or assisted, by the polymerization initiator or rate modifier that was previously loaded on the flexible material.

The polymerizable (i.e., monomer and/or prepolymeric) adhesive composition may include one or more polymerizable monomers, which preferably are synthetic or semi-synthetic monomers. Preferred monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. Nos. 5,328,687, 5,928,611 and 6,183,593, U.S. patent application Ser. No. 09/430,177, filed on Oct. 29, 1999, and U.S. Pat. No. 6,183,593, which are hereby incorporated in their entirety by reference herein.

Preferred monomers include 1,1-disubstituted ethylene monomers, such as α-cyanoacrylates including, but not limited to, alkyl α-cyanoacrylates having an alkyl chain length of from about 1 to about 20 carbon atoms or more, preferably from about 3 to about 8 carbon atoms.

The ca-cyanoacrylates of the present invention can be prepared according to several methods known in the art. U.S. Pat. Nos. 2,721,858, 3,254,111, 3,995,641, and 4,364,876, each of which is hereby incorporated in its entirety by reference herein, disclose methods for preparing α-cyanoacrylates.

Preferred α-cyanoacrylate monomers used in this invention include methyl cyanoacrylate, ethyl cyanoacrylate, n-butyl cyanoacrylate, 2-octyl cyanoacrylate, methoxyethyl cyanoacrylate, ethoxyethyl cyanoacrylate, dodecyl cyanoacrylate, 2-ethylhexyl cyanoacrylate, butyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, hexyl cyanoacrylate, or dodecylcyanoacrylate.

Other suitable cyanoacrylates for use in the present invention also include, but are not limited to, alkyl ester cyanoacrylate monomers such as those having the formula

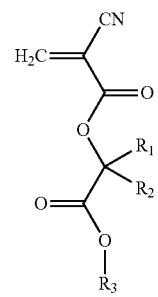

wherein $R_1$ and $R_2$ are, independently H, a straight, branched or cyclic alkyl, or are combined together in a cyclic alkyl group, and $R_3$ is a straight, branched or cyclic alkyl group. Preferably, $R_1$ is H or a $C_1$, $C_2$ or $C_3$ alkyl group, such as methyl or ethyl; $R_2$ is H or a $C_1$, $C_2$ or $C_3$ alkyl group, such as methyl or ethyl; and $R_3$ is a $C_1$-$C_{16}$ alkyl group, more preferably a $C_1$-$C_{10}$ alkyl group, such as methyl, ethyl, propyl, butyl, pentyl, hexyl, heptyl, octyl, nonyl or decyl, and even more preferably a $C_2$, $C_3$ or $C_4$ alkyl group. Such alkyl ester cyanoacrylates and other suitable monomers are disclosed in, for example, U.S. patent application Ser. No. 09/919,877, filed Aug. 2, 2001, and U.S. Pat. No. 6,620,846, the entire disclosures of which are incorporated herein by reference.

Examples of preferred alkyl ester cyanoacrylates include, but are not limited to, butyl lactoyl cyanoacrylate (BLCA), butyl glycoloyl cyanoacrylate (BGCA), ethyl lactoyl cyanoacrylate (ELCA), and ethyl glycoloyl cyanoacrylate (EGCA). BLCA may be represented by the above formula, wherein $R_1$ is H, $R_2$ is methyl and $R_3$ is butyl. BGCA may be represented by the above formula, wherein $R_1$ is H, $R_2$ is H and $R_3$ is butyl. ELCA may be represented by the above formula, wherein $R_1$ is H, $R_2$ is methyl and $R_3$ is ethyl. EGCA may be represented by the above formula, wherein $R_1$ is H, $R_2$ is H and $R_3$ is ethyl.

The composition may optionally also include at least one other plasticizing agent that assists in imparting flexibility to the polymer formed from the monomer. The plasticizing agent preferably contains little or no moisture and should not significantly affect the stability or polymerization of the monomer. Examples of suitable plasticizers include but are not limited to tributyl citrate, acetyl tri-n-butyl citrate (ATBC), polymethylmethacrylate, polydimethylsiloxane, hexadimethylsilazane and others as listed in U.S. Pat. No. 6,183,593, the disclosure of which is incorporated in its entirety by reference herein.

The composition may also optionally include at least one thixotropic agent. Suitable thixotropic agents are known to the skilled artisan and include, but are not limited to, silica gels such as those treated with a silyl isocyanate, and optionally surface treated titanium dioxide. Examples of suitable thixotropic agents and thickeners are disclosed in, for example, U.S. Pat. Nos. 4,720,513, and 6,310,166, the disclosures of which are hereby incorporated in their entireties by reference herein.

The composition may optionally also include thickeners. Suitable thickeners may include poly (2-ethylhexy methacrylate), poly(2-ethylhexyl acrylate) and others as listed in U.S. Pat. No. 6,183,593, the disclosure of which is incorporated by reference herein in its entirety.

The composition may also optionally include at least one natural or synthetic rubber to impart impact resistance. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties by reference herein.

The composition may optionally also include one or more stabilizers, preferably both at least one anionic vapor phase stabilizer and at least one anionic liquid phase stabilizer. These stabilizing agents may inhibit premature polymerization. Suitable stabilizers may include those listed in U.S. Pat. No. 6,183,593, the disclosure of which is incorporated by reference herein in its entirety. Furthermore, certain stabilizers may also function as anti-microbial agents, such as, for example, various acidic anti-microbials, as identified above.

The compositions may also include pH modifiers to control the rate of degradation of the resulting polymer, as disclosed in U.S. Pat. No. 6,143,352, the entire disclosure of which is hereby incorporated by reference herein in its entirety.

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated herein in its entirety by reference, discloses exemplary cross-linking agents.

The compositions of this invention may further contain colorants such as dyes, pigments, and pigment dyes.

The polymerizable compositions useful in the present invention may also further contain one or more preservatives, for prolonging the storage life of the composition. Suitable preservatives, and methods for selecting them and incorporating them into adhesive compositions, are disclosed in U.S. patent application Ser. No. 09/430,180, the entire disclosure of which is incorporated herein by reference. Such preservatives can be in addition to any anti-microbial agent that may or may not be added to the composition. Such preservatives can be included irrespective of whether the composition and containers are sterilized.

In embodiments, the materials and processes of the present invention provide significant advantages over the current materials and methods for wound closure. These advantages include, among others, improved wound closure, improved wound approximation, improved strength, ability to use on longer wounds, less run-off of adhesive, longer working time, provision of an improved durable microbial barrier, reduced procedure time, improved cosmesis, less pain (during staple/suture removal) resulting in increased patient satisfaction, and improved financial/economic outcomes by eliminating follow-up visits for staple/suture removal.

The materials and processes of the present invention provide improved wound closure. Because the composite structure provides a flexible polymeric covering over the wound site, it provides a degree of tension to assist in closing the wound and maintain the wound closed. By a combination of the flexible material within the composite structure, and the rigidity and adhesion provided by polymerization of the polymerizable adhesive composition, the composite structure provides improved strength, decreases wound dehiscence, and assists healing.

The materials and processes of the present invention also provide an improved microbial barrier. Because the composite structure fully covers the wound, microbial transport into and out of the wound are decreased. This in turn helps battle or prevent infection, in turn resulting in faster wound healing.

The materials and processes of the present invention also provide improved cosmesis. Such cosmesis benefits includes improved cosmetic appearances both during and after the wound healing process. For example, during wound healing, the composite structures of the present invention provide decreased dressing bulk and thickness and improved appearance. Furthermore, because the composite structures permit more precise and sustained wound approximation, the composite structures can provide decreased scar appearance, such as in terms of scar width, scar tissue height, scar coloration, and the like.

Related to the above advantages, the materials and processes of the present invention provide increased patient satisfaction. Increased satisfaction is provided, for example, due to the improved cosmetic results, and improved assurance of wound closure and dressing strength, and the like. In addition, because of the strong bond provided, the composite structure of the present invention is expected to remain in place over an external wound for about 10 to 14 days, although shorter or longer times may be provided. During that time, the patient can bathe without worrying about water and contaminants entering the wound through the dressing. Furthermore, because staple or suture removal is not required, the patient experiences less pain and anticipation, improving the healing experience.

The present invention is thus applicable to a wide range of treatments, including wound treatment and other medical procedures. For example, the present invention can be used as a replacement for, or in addition to, sutures or staples to join together two surfaces. The invention can also be used to coat, protect, or otherwise cover surface, superficial, internal, or topical wounds including, but not limited to, minor cuts, scrapes, irritations, compromised skin, superficial lacerations, abrasions, burns, sores, and stomatitis. The methods of the invention can also be used on tissues that do not show any signs of tissue damage. For example, the methods can be used to deliver medicaments to a patient through healthy tissue. They can also be used, for example, to locally deliver medicaments to tissues such as tumors or organs.

Specific embodiments of the invention will now be described in detail. These Examples are intended to be illustrative, and the invention is not limited to the materials, conditions, or process parameters set forth in these embodiments. All parts and percentages are by weight unless otherwise indicated.

EXAMPLES

Example 1

The working and setting times of the inventive composite device, using a flexible textile material and a cyanoacrylate polymerizable adhesive formulation, are compared to the working and setting times of conventional available cyanoacrylate devices. The conventional available cyanoacrylate devices used ire the DERMABOND® topical skin adhesive products comprising a polymerizable monomer dispersed from an applicator having a porous tip containing polymerization initiator. Two DERMABOND® adhesive formulations are tested namely, a low viscosity adhesive formulation, referred to here as DERMABOND LV and a high viscosity adhesive formulation, referred to here as DERMABOND HV (both manufactured by Closure Medical Corporation and available from Ethicon). The composite devices of the present invention are also prepared using the cyanoacrylate polymerizable adhesive compositions of the DERMABOND LV and DERMABOND HV formulations, with the cyanoacrylate polymerizable adhesive compositions being extracted from the commercial applicators so that the composition does not contact polymerization initiator that is present in the applicator tips. These extracted cyanoacrylate polymerizable adhesive compositions are referred to here as "composite adhesive formulations".

Working time is a measurement of the time during which the polymerizable adhesive composition can be expressed as a liquid from the application device. Once the working time has expired, the adhesive has polymerized within the applicator, clogging or plugging the applicator tip. Setting time is the time required for the adhesive to polymerize on a substrate once it has been applied.

Synthetic SPECTRA MESH® filtration material (available from Spectrum Laboratories, Inc.), a textile with 70 μm pores (openings) and an open area of 36%, is cut into strips 1.0 cm×3.75 cm. Benzyldimethylhexa-decylammonium chloride (BHC) initiator is immobilized within the textile by dipping the strips of textile in either 0.1 M or 0.15 M solutions of BHC in methanol. Each strip is fully saturated with initiator solution by dipping for 2 to 3 seconds. Following dipping, the textile strips are placed onto a polyethylene board and allowed to air-dry for at least 24 hours at 25° C.

The DERMABOND LV and DERMABOND HV adhesive formulations and the composite adhesive formulations are tested by applying them to poly(vinyl chloride) (PVC) slides heated to 31.5° C.±1.5° C. The slides are used in concert with a thermocouple data acquisition apparatus, which is used to monitor setting time and temperature of the samples.

For evaluation of setting times, DERMABOND LV adhesive formulation is applied to the PVC slides in a thin layer using the commercially-available DERMABOND® applicator that includes a porous tip loaded with initiator for initiation of the adhesive polymerization. Setting times and temperatures are determined for 10 samples. Working times are determined by inspection. Similarly, DERMABOND HV adhesive formulation setting time is tested and data is acquired for 10 samples. The results are shown in Table 2 below.

The setting and working times of adhesive formulations of four composite devices are also investigated: (1) DERMABOND LV adhesive formulation and SPECTRA MESH® filtration material dipped in 0.1 M BHC solution (Composite A); (2) DERMABOND LV adhesive formulation and SPECTRA MESH® filtration material dipped in 0.15 M BHC solution (Composite B); (3) DERMABOND HV adhesive formulation and SPECTRA MESH® filtration material dipped in 0.15 M BHC solution (Composite C); and, (4) DERMABOND LV adhesive formulation and SPECTRA MESH® filtration material used as-received, without the addition of BHC initiator (Composite Control). In the composite formulations, the DERMABOND LV and DERMABOND HV adhesive formulations used are the same as those formulations found in the commercial DERMABOND LV adhesive applicator and the DERMABOND HV applicator, however, when testing the composite adhesive formulations, these adhesives are used without initiation by an applicator device including an initiated porous tip. Instead, a pipetter is used to dispense the adhesives, and initiation of the adhesive polymerization is accomplished by the BHC initiator immobilized within the nylon mesh. The components of the composite devices are summarized in the following Table 1.

TABLE 1

Composite Devices

| Sample | Flexible Material | Imitator Solution Applied to Flexible Material | Adhesive Composition |
|---|---|---|---|
| DERMABOND LV | None | None | DERMABOND LV (applicator initiated) |
| DERMABOND LV | None | None | DERMABOND HV (applicator initiated) |
| Composite A | SPECTRA MESH ® | 0.1M BHC | DERMABOND LV |
| Composite B | SPECTRA MESH ® | 0.15M BHC | DERMABOND LV |
| Composite C | SPECTRA MESH ® | 0.16M BHC | DERMABOND HV |

TABLE 1-continued

Composite Devices

| Sample | Flexible Material | Imitator Solution Applied to Flexible Material | Adhesive Composition |
|---|---|---|---|
| Composite Control | SPECTRA MESH® | None | DERMABOND LV |

During composite formulation testing, 75 μL of adhesive is pipetted onto the center of each mesh test strip. Nineteen (19) samples are tested for Composite A, 20 samples for Composite B, 10 samples for Composite C, and 20 samples for the composite control. The thermocouple data acquisition apparatus is used to monitor setting time and temperature as with the DERMABOND LV and DERMABOND HV samples. Working times are determined by inspection.

TABLE 2

Testing Results

| Formulation | Working Time | Setting Time (sec) | Setting Temperature (° C.) |
|---|---|---|---|
| DERMABOND LV | <3 min | 74.9 ± 20.8 | 44.2 ± 4.0 |
| DERMABOND HV | <3 min | 110.1 ± 18.9 | 50.0 ± 6.3 |
| Composite A | >8 hours | 32.7 ± 6.3 | 47.1 ± 5.5 |
| Composite B | >8 hours | 30.9 ± 4.8 | 49.2 ± 5.7 |
| Composite C | >8 hours | 49.6 ± 10.2 | 50.1 ± 5.9 |
| Composite Control | >8 hours | >5400 | ND (non-detectable) |

Evaluation of the data presented in the table reveals the effects of the initiation method used in the cyanoacrylate textile (mesh) composite on both working and setting times, and the resulting composite structure. Initiation of the adhesive polymerization using initiator immobilized within the mesh, instead of initiator contained within a porous applicator tip, dramatically increases the working time of the adhesive. Commercially-available DERMABOND® adhesive applicators have a working time that is determined by the polymerization time of the adhesive within the initiated applicator. The inventive composite formulation does not require an initiated application tip. The initiator is present within the mesh, and initiation of the adhesive occurs only on the substrate when adhesive is applied to the mesh. Adhesive can be applied to the mesh at any desired rate, and it will remain liquid in the applicator for a much longer period of time than it would in an adhesive applicator that includes initiator in an applicator tip.

Setting time is also dramatically affected by the initiation method of the inventive adhesive mesh composite. The setting times of Composite A and Composite B are approximately 50% the setting time of DERMABOND LV adhesive and approximately 30% the setting time of DERMABOND HV adhesive. Composite C shows similarly dramatic results. Setting times are lowered in the composites without increasing setting temperatures, something that would not be possible using conventional application devices that include initiator in the applicator tip. To decrease setting time using current applicator technology, the amount of initiator in the porous applicator tip would have to be significantly increased, which would be accompanied by a concomitant increase in the associated setting temperature. Having initiator evenly distributed throughout the textile alters initiation and polymerization kinetics, facilitating more efficient initiator-adhesive mixing. This improved mixing configuration serves to lower setting times while maintaining low setting temperatures. In addition, this mixing configuration enables improved control of setting time and temperature through controlled distribution of initiator within the composite. As a result, the composite structure can be formed as a wound covering and closure device in a manner that is quick (i.e., that has a fast setting time) and easier to apply (longer working time), but which remain comfortable to the patient (i.e., as not having a significantly high setting temperature).

The above improvements provided by the present invention also provide valuable benefits to medical professionals or other using the methods and devices of the invention. For example, the faster setting time enables medical professionals to apply the composite structure as a wound closure device much faster than previously possible, freeing up the medical professional to proceed to other tasks and to speed the treatment process, providing faster and more efficient procedures. This in turn could result in lower operating room and treatment costs, and reduced patient and insurance charges.

Example 2

The tensile strength of film samples of DERMABOND LV adhesive are compared to the tensile strength of Composite A, described in Example 1 above.

Thin films of DERMABOND LV adhesive are prepared by expressing the adhesive from a DERMABOND LV applicator onto a glass plate. Subsequently, a second glass plate of the same size is placed on top of the adhesive such that the adhesive is pressed between the two plates. Once the adhesive polymerizes, the glass plates are separated and the film of adhesive is removed. This film was then cut into strips with dimensions 4.0 inch×0.5 inch. Ten DERMABOND LV film strips are thus prepared.

Strips of Composite A are prepared using SPECTRA MESH® filtration material loaded with initiator by dip coating in an 0.1 M solution of BHC in methanol, as described above. Dip coated strips are allowed to dry for 24 hours prior to their use. Mesh strips, measuring 4.0 inch×0.5 inches, are saturated with DERMABOND LV adhesive by expressing the adhesive from a pipetter onto the strips in the same manner as in Example 1. By this method, 10 strips of Composite A are prepared.

An MTS Sintech 2/G apparatus is used for tensile testing. Prior to testing, all film samples are stored at 25° C. for at least 4 hours. The dimensions of each sample are measured 3 times before testing, and the average values are determined. The average width of the DERMABOND LV adhesive films is 0.513 inch and the average thickness is 0.009 inch. The average width of the Composite A strips is 0.494 inch and the average thickness is 0.014 inch. The tensile strengths of the DERMABOND LV adhesive strips and the Composite A strips are tested by pulling the strips to failure by breakage using a gauge length of 1.0 inch and a crosshead speed of 3.0 inch per minute. The tensile strength data is shown in Table 3 below:

TABLE 3

| Sample | Tensile Strength Results | | |
|---|---|---|---|
| | Stress at Break (PSI) | Elongation at Break (in) | Strain at Break (%) |
| DERMABOND LV | 615.3 ± 123.3 | 3.07 ± 1.03 | 301.8 ± 101.3 |
| Composite A | 1932.6 ± 298.2 | 0.38 ± 0.05 | 37.2 ± 5.2 |

Review of the tensile strength data reveals the dramatically higher tensile strength of Composite A in comparison to DERMABOND LV adhesive film. Formation of a composite adhesive by the method used for Composite A results in a stress at break (i.e., the amount of stress applied immediately before sample breaks) for that composite that is more than 300% that of the DERMABOND LV adhesive film. The strain at break for Composite A is also dramatically different than that of DERMABOND LV adhesive film, its value being approximately 12% of that of the strain at break value for DERMABOND LV. This data demonstrates that composite structures of the present invention have distinctively different mechanical properties than films of commercially-available DERMABOND LV adhesive.

While the invention has been described with reference to preferred embodiments, the invention is not limited to the specific examples given, and other embodiments and modifications can be made by those skilled in the art without departing from the spirit and scope of the invention.

We claim:

1. A method of bonding, comprising:
   placing a flexible material over a substrate, wherein a polymerization initiator or rate modifier disposed in or on said flexible material;
   applying a polymerizable adhesive composition over and substantially covering at least a portion of the flexible material; and
   allowing the polymerizable adhesive composition to permeate into and under the flexible material and polymerize to form a composite structure bonded to said substrate.

2. The method of claim 1, wherein said polymerization initiator or rate modifier is a polymerization initiator or rate modifier for said polymerizable adhesive composition.

3. The method of claim 1, wherein said substrate is tissue.

4. The method of claim 1, wherein said tissue is selected from the group consisting of bone, organ surfaces, skin, and mucous membranes.

5. The method of claim 1, wherein said substrate is tissue is internal tissue.

6. The method of claim 1, wherein said substrate is tissue is external tissue.

7. The method of claim 1, wherein said substrate is a section of tissue that includes a wound to be closed.

8. The method of claim 7, wherein said flexible material fully covers said wound.

9. The method of claim 1, wherein said applying comprises:
   placing a quantity of said polymerizable adhesive composition on an exposed side of the flexible material; and
   spreading the quantity of polymerizable adhesive composition to substantially cover the flexible material.

10. The method of claim 1, further comprising applying a polymerizable adhesive composition to said substrate prior to placing said flexible material over said substrate.

* * * * *